US006291523B1

(12) United States Patent
Fujimoto et al.

(10) Patent No.: US 6,291,523 B1
(45) Date of Patent: Sep. 18, 2001

(54) CERTAIN 5-ALKYL-2-ARYLAMINOPHENYLACETIC ACIDS AND DERIVATIVES

(75) Inventors: Roger A. Fujimoto, Morristown; Leslie W. McQuire, Warren; Benjamin B. Mugrage, Basking Ridge; John H. van Duzer, Asbury; Daqiang Xu, Whippany, all of NJ (US)

(73) Assignee: Novartis AG, Basel (CH)

( * ) Notice: Subject to any disclaimer, the term of this patent is extended or adjusted under 35 U.S.C. 154(b) by 24 days.

(21) Appl. No.: 09/139,254

(22) Filed: Aug. 25, 1998

Related U.S. Application Data
(60) Provisional application No. 60/069,837, filed on Aug. 28, 1997, and provisional application No. 60/057,803, filed on Aug. 28, 1997.

(51) Int. Cl.$^7$ .......................... A61K 31/216; C07C 229/42
(52) U.S. Cl. ........................... 514/533; 514/567; 560/45; 560/47; 560/48
(58) Field of Search ........................ 514/533, 567; 560/45, 47, 48

(56) References Cited

U.S. PATENT DOCUMENTS

| | | |
|---|---|---|
| 3,531,493 | 9/1970 | Gittos et al. . |
| 3,558,690 | 1/1971 | Sallmann et al. . |
| 3,652,762 | 3/1972 | Sallmann et al. . |
| 3,895,063 | 7/1975 | Sallmann et al. . |
| 4,173,577 | 11/1979 | Sallmann et al. . |
| 4,548,952 | 10/1985 | Casas . |
| 5,958,978 | 9/1999 | Yamazaki et al. . |

FOREIGN PATENT DOCUMENTS

| | | |
|---|---|---|
| 3445011 | 6/1985 | (DE) . |
| 3445011 A1 | 6/1985 | (DE) . |
| 865788 A1 | 9/1998 | (EP) . |
| WO 94/04484 | 3/1994 | (WO) . |
| WO 96/00716 | 1/1996 | (WO) . |
| WO 97/09977 | 3/1997 | (WO) . |

OTHER PUBLICATIONS

Chemical Abstract 118: 80787 (1993).
Chemical Abstracts 104: 109230 (Abstract of DE 3445011).
Griswold et al., Medicinal Research Reviews, vol. 16, No. 2, pp. 181–206 (1996).
Moser et al., J. Med. Chem., vol. 33, pp. 2358–2368 (1990).
Sircar J.C., Curr.Opin.Invest.Drugs, vol. 2 (4), pp. 403–407 (1993).
Englehardt G., Z. Rheumatol, vol. 53, Suppl. 1, p. 68 (1994).
Englehardt G., Eur. J., Clin. Pharmacology, vol. 47 (No. 1) p. A98 (1994).
Brit. J. Pharmacol., vol. 112, Proc. Suppl., p. 183P (1994).
Klein T. et al., Biochemical Pharmacology, vol. 48, No. 8, pp 1605–1610 (1994).
Mitchell J.A. et al., Proc.Natl.Acad.Sci.USA, vol. 90, pp. 11693–11697 (1994).
Pallapies D. et al., Life Sciences, vol. 57, No. 2, pp. 83–89 (1995).
Pairet M. et al., Proceedings of a conference, Oct. 10–11, 1995, "Improved Non–Steroid Anti–Inflammatory Drugs COX–2 Enzyme Inhibitors", Edited by John Vane et al., pp. 103–119.
Seibert K. et al., Advances in Prostaglandin, Thromboxane, and Leukotriene Research, vol. 23, p. 125–127 (1995).
Englehardt G., Br.J.Rheumatol. vol. 34, Abstr. Suppl. 1, p. 48 (1995).
Glaser K.B., Inflammopharmacology, vol. 3, pp. 335–345, (1995).
Gierse J.K. et al., Biochem.J., vol. 305, pp. 479–484 (1995).
Prasit P. et al., Med.Chem.Res., vol. 5, pp. 364–374 (1995).
Chan Chi–Chung et al., Journ.Pharmacology and Experimental Therapeutics, vol. 274, pp. 1531–1537 (1995).
Grossman C.J. et al., Inflammation Res., vol. 44, pp. 253–257 (1995).
Glaser K.B. et al., Inflammation Res., vol. 44, Suppl. 3, p. S276 (1995).
Grossman C.J. et al., Inflammation Res., vol. 44, Suppl. 3, p. S272 (1995).
Warner T.D. et al., Inflammation Res., vol. 44, Suppl. 3, p. S274 (1995).
Terlain B. et al., Presse Med., vol. 24, No. 10, pp. 491–496 (1995).
Gierse J.K. et al., Journ.Biological Chemistry, vol. 271, No. 26, pp. 15810–15814 (1996).
Englehardt G., Z. Rheumatol. vol. 55, Suppl. 1, p. 112 (1996).

(List continued on next page.)

*Primary Examiner*—Robert Gerstl
(74) *Attorney, Agent, or Firm*—Norbert Gruenfeld

(57) ABSTRACT

Disclosed are the compounds of formula I

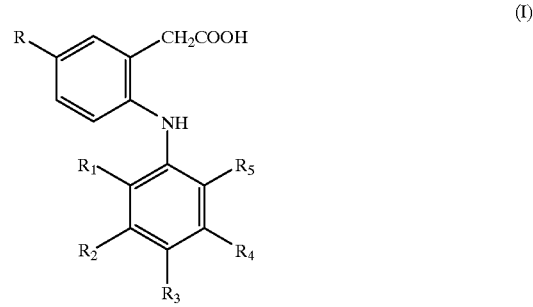

wherein R is methyl or ethyl; $R_1$ is chloro or fluoro; $R_2$ is hydrogen or fluoro; $R_3$ is hydrogen, fluoro, chloro, methyl, ethyl, methoxy, ethoxy or hydroxy; $R_4$ is hydrogen or fluoro; and $R_5$ is chloro, fluoro, trifluoromethyl or methyl; and pharmaceutically acceptable salts thereof, as selective COX-2 cyclooxygenase inhibitors; and pharmaceutically acceptable prodrug esters thereof.

36 Claims, No Drawings

OTHER PUBLICATIONS

Distel M. et al., British Jour. of Rheumatology, vol. 35 (suppl. 1) pp. 68–77 (1996).

Churchill L. et al., Inflammopharmacology, vol. 4, pp. 125–135 (1996).

Steinhilber D., Pharm.Ztg., vol. 141(37), pp. 11–18 (1996).

Vane J.R. et al., Scan.J.Rheumatol. vol. 25 (Suppl. 102) pp. 9–21 (1996).

Matsushita M. et al., Inflamm.Res., vol. 46, pp. 461–466 (1997).

Englehardt G. et al., Biochemical Pharmacology, vol. 51, pp. 21–28 (1996).

Cromlish W.A. et al., Biochemical Pharmacology, vol. 52, pp. 1777–1785 (1996).

Brideau C. et al., Inflamm.Res., vol. 45, pp. 68–74 (1996).

Patrignani P. et al., Journal of Physiology and Pharmacology, vol. 48, 4, pp. 623–631 (1997).

Pairet M. et al., Proceedings of a conference on Mar. 20–21, 1997, "Selective COX–2 Inhibitors Pharmacology, Clinical Effects and Therapeutic Potential" Edited by John Vane et al., pp. 27–46.

Dammann H.G. et al., Clinical Pharmacology & Therapeutics, vol. 61, p. 162 (1997).

Pairet M. et al., Infamm. Res., vol. 47, Suppl. 2, pp. S93–S101 (1998).

Silvestre J. et al., Drugs of the Future, vol. 23(6), pp. 598–601 (1998).

Giuliano F. et al., Brit. J.Pharmacol., vol. 125, Suppl. 1, 35P (1998).

Simmons D.L. et al., Journal of Lipid Mediators, vol. 6, pp. 113–117 (1993).

Japanese Pharmacol. Ther., vol. 25, No. 8, pp. 2131–2136 (1997).

Japanese Journal of Inflammation, vol. 15, No. 5, pp. 409–411 (1995).

Cryer B. et al., Amer.J.Med., vol. 104, No. 5, pp. 413–421 (1998).

CERTAIN 5-ALKYL-2-ARYLAMINOPHENYLACETIC ACIDS AND DERIVATIVES

CROSS-REFERENCE TO RELATED APPLICATIONS

This application claims the benefit of U.S. provisional application No. 60/069,837 filed Aug. 28, 1997 and of U.S. provisional application No. 60/057,803 filed Aug. 28, 1997.

BACKGROUND AND SUMMARY OF THE INVENTION

The invention relates to 5-alkyl-2-arylaminophenylacetic acids and derivatives thereof as defined herein which are particularly potent and selective cyclooxygenase-2(COX-2) inhibitors, methods for preparation thereof, pharmaceutical compositions comprising said compounds, methods of selectively inhibiting COX-2 activity and of treating conditions in mammals which are responsive to COX-2 inhibition using said compounds or pharmaceutical compositions comprising said compounds of the invention.

Various substituted 2-arylaminophenylacetic acids and derivatives thereof have been disclosed e.g. in J. Med. Chem. 33, 2358 (1990), U.S. Pat. Nos. 3,558,690, 3,652,762, 4,173,577 and 4,548,952, and in PCT applications WO 94/104484, WO 97/09977, WO 96/00716 and DE 13,445,011 as analgesic agents, non-steroidal antiinflammatory agents and cyclooxygenase inhibitors. As to 5-alkyl-2-arylaminophenylacetic acids, the only example known to be described in the literature is 5-methyl-2-(2,6-dimethylanilino)-phenylacetic acid and its sodium salt (U.S. Pat. No. 3,558,690) for which no biological data has been reported.

2-(2,6-Dichlorophenylamino) phenylacetoxyacetic acid (aceclofenac) and salts thereof have been disclosed e.g. in U.S. Pat. No. 4,548,952, and in PCT application WO 96/00716 as non-steroidal antiinflammatory and analgesic agents. The pharmacological properties of aceclofenac are apparently the result of in vivo conversion to diclofenac and/or derivatives thereof.

Non-steroidal antiinflammatory agents block prostaglandin synthesis by inhibition of the enzyme cyclooxygenase. Cyclooxygenase is now known to comprise a constitutive isoform (cyclooxygenase-1, COX-1) and an inducible isoform (cyclooxygenase-2, COX-2). COX-1 appears responsible for protective beneficial features of prostaglandins, e.g. for the gastrointestinal tract, kidney, etc., while the inducible isoform COX-2 appears responsible for pathological conditions associated with prostaglandins, such as inflammatory conditions. A limitation to the use of conventional nonsteroidal antiinflammatory drugs (NSAIDS), including aceclofenac and diclofenac sodium which is the sodium salt of 2,6-dichloroanilinophenylacetic acid, is gastrointestinal toxicity now attributed to the inhibition of the COX-1 isoform of cyclooxygenase. Selective inhibition of inducible COX-2 in vivo has been reported to be antiinflammatory and non-ulcerogenic (Proc. Natl. Acad. Sci. (U.S.A.) 1994; 91:3228–3232).

The present invention provides novel 5-alkyl substituted 2-arylaminophenylacetic acids and derivatives which surprisingly inhibit COX-2 without significantly inhibiting COX-1. The invention thus provides novel nonsteroidal antiinflammatory agents which are surprisingly free of undesirable side effects usually associated with the classical nonsteroidal antiinflammatory agents, such as gastrointestinal and renal side effects. The compounds of the present invention are thus particularly useful or may be metabolically converted to compounds which are particularly useful as COX-2 selective cyclooxygenase inhibitors. They are thus particularly useful for the treatment of cyclooxygenase-2 dependent disorders in mammals, including inflammation, pyresis, pain, osteoarthritis, rheumatoid arthritis, migraine headache, cancer such as digestive tract (e.g. colon) cancer and melanoma, neurodegenerative diseases (such as multiple sclerosis), Alzheimer's disease, osteoporosis, asthma, lupus and psoriasis while substantially eliminating undesirable gastrointestinal ulceration associated with conventional cyclooxygenase inhibitors. The compounds of the invention are also UV absorbers, in particular UV-B absorbers, and are useful for blocking or absorbing UV radiation, for instance for the treatment and prevention of sunburn, e.g. in suntan products.

Ocular applications of the compounds of the invention include the treatment of ocular inflammation, of ocular pain including pain associated with ocular surgery such as PRK or cataract surgery, of ocular allergy, of photophobia of various etiology, of elevated intraocular pressure (in glaucoma) by inhibiting the production of trabecular meshwork inducible glucocorticoid response (TIGR) protein and of dry eye disease.

The compounds of the present invention are useful for the treatment of neoplasia particularly neoplasia that produce prostaglandins or express cyclooxygenase, including both benign and cancerous tumors, growths and polyps, in particular epithelium cell-derived neoplasia. Compounds of the present invention are in particular useful for the treatment of liver, bladder, pancreatic, ovarian, prostate, cervical, lung and breast cancer and, especially gastrointestinal cancer, for example cancer of the colon, and skin cancer, for example squamous cell or basal cell cancers and melanoma, as indicated above.

The term "treatment" as used herein is to be understood as including both therapeutic and prophylactic modes of therapy, e.g. in relation to the treatment of neoplasia, therapy to prevent the onset of clinically or preclinically evident neoplasia, or for the prevention of initiation of malignant cells or to arrest or reverse the progression of premalignant to malignant cells, as well as the prevention or inhibition of neoplasia growth or metastasis. In this context, the present invention is, in particular, to be understood as embracing the use of compounds of the present invention to inhibit or prevent development of skin cancer, e.g. squamous or basal cell carcinoma consequential to UV light exposure, e.g. resulting from chronic exposure to the sun.

DETAILED DESCRIPTION OF THE INVENTION

The invention relates to compounds of formula I

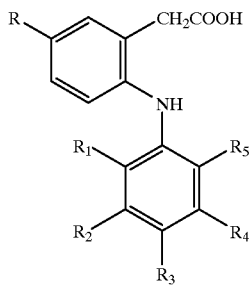

wherein R is methyl or ethyl;
$R_1$ is chloro or fluoro;
$R_2$ is hydrogen or fluoro;
$R_3$ is hydrogen, fluoro, chloro, methyl, ethyl, methoxy, ethoxy or hydroxy;
$R_4$ is hydrogen or fluoro; and
$R_5$ is chloro, fluoro, trifluoromethyl or methyl;
pharmaceutically acceptable salts thereof; and
pharmaceutically acceptable prodrug esters thereof.

A particular embodiment of the invention relates to the compounds of formula I wherein R is methyl or ethyl; $R_1$ is chloro or fluoro; $R_2$ is hydrogen; $R_3$ is hydrogen, fluoro, chloro, methyl or hydroxy; $R_4$ is hydrogen; and $R_5$ is chloro, fluoro or methyl; pharmaceutically acceptable salts thereof, and pharmaceutically acceptable prodrug esters thereof.

A preferred embodiment relates to the compounds of formula I wherein R is methyl or ethyl; $R_1$ is fluoro; $R_2$ is hydrogen; $R_3$ is hydrogen, fluoro or hydroxy; $R_4$ is hydrogen; and $R_5$ is chloro; pharmaceutically acceptable salts thereof; and pharmaceutically acceptable prodrug esters thereof.

Another preferred embodiment of the invention relates to compound of formula I wherein R is ethyl or methyl; $R_1$ is fluoro; $R_2$ is hydrogen or fluoro; $R_3$ is hydrogen, fluoro, ethoxy or hydroxy; $R_4$ is hydrogen or fluoro; and $R_5$ is chloro, fluoro or methyl; pharmaceutically acceptable salts thereof; and pharmaceutically acceptable prodrug esters thereof.

Further preferred are said compounds wherein R is methyl or ethyl; $R_1$ is fluoro; $R_2$–$R_4$ are hydrogen or fluoro; and $R_5$ is chloro or fluoro; pharmaceutically acceptable salts thereof; and pharmaceutically acceptable prodrug esters thereof.

A further embodiment of the invention relates to the compounds of formula I wherein R is methyl or ethyl; $R_1$ is fluoro; $R_2$ is fluoro; $R_3$ is hydrogen, ethoxy or hydroxy; $R_4$ is fluoro; and $R_5$ is fluoro; pharmaceutically acceptable salts thereof; and pharmaceutically acceptable prodrug esters thereof.

Another preferred embodiment of the invention relates to the compounds of formula I wherein R is methyl; $R_1$ is fluoro; $R_2$ is hydrogen; $R_3$ is hydrogen or fluoro; $R_4$ is hydrogen; and $R_5$ is chloro; pharmaceutically acceptable salts thereof; and pharmaceutically acceptable prodrug esters thereof. Particular embodiments of the invention relate to compounds of formula I (a) wherein R is methyl; $R_1$ is fluoro; $R_2$ is hydrogen; $R_3$ is hydrogen; $R_4$ is hydrogen; and $R_5$ is chloro; pharmaceutically acceptable salts thereof; and pharmaceutically acceptable prodrug esters thereof, (b) wherein R is methyl; $R_1$ is fluoro; $R_2$ is hydrogen; $R_3$ is fluoro; $R_4$ is hydrogen; and $R_5$ is chloro; pharmaceutically acceptable salts thereof; and pharmaceutically acceptable prodrug esters thereof;

(c) wherein R is ethyl; $R_1$ is fluoro; $R_2$ is fluoro; $R_3$ is hydrogen; $R_4$ is fluoro; and $R_5$ is fluoro; pharmaceutically acceptable salts thereof; and pharmaceutically acceptable prodrug esters thereof; and (d) wherein R is ethyl; $R_1$ is chloro; $R_2$ is hydrogen; $R_3$ is chloro; $R_4$ is hydrogen; and $R_5$ is methyl; pharmaceutically acceptable salts thereof; and pharmaceutically acceptable prodrug esters thereof.

The general definitions used herein have the following meaning within the scope of the present invention.

Pharmaceutically acceptable prodrug esters are ester derivatives which are convertible by solvolysis or under physiological conditions to the free carboxylic acids of formula I. Such esters are e.g. lower alkyl esters (such as the methyl or ethyl ester), carboxy-lower alkyl esters such as the carboxymethyl ester, nitrooxy-lower alkyl esters (such as the 4-nitrooxybutyl ester), and the like. Preferred are the 5-alkyl substituted 2-arylaminophenylacetoxyacetic acids of formula Ia

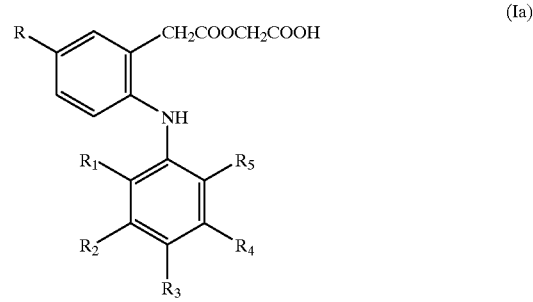

wherein R and $R_1$–$R_5$ have meaning as defined hereinabove for compounds of formula I; and pharmaceutically acceptable salts thereof.

Pharmaceutically acceptable salts represent metal salts, such as alkaline metal salts, e.g. sodium, potassium, magnesium or calcium salts, as well as ammonium salts, which are formed e.g. with ammonia and mono- or di-alkylamines, such as diethylammonium salts, and with amino acids, such as arginine and histidine salts.

A lower alkyl group contains up to 7 carbon atoms, preferably 1 to 4 carbon atoms and represents for example methyl, ethyl, propyl or butyl, and may be straight chain or branched.

The compounds of the invention are useful as selective cyclooxygenase-2 inhibitors or as prodrugs thereof. The selective cyclooxygenase-2 (COX-2) inhibitors and prodrugs thereof of the invention are particularly useful for the treatment of e.g. inflammation, pyresis, pain, osteoarthritis, rheumatoid arthritis and other conditions responsive to the inhibition of cyclooxygenase-2 and are typically substantially free of undesirable gastrointestinal side effects associated with conventional non-steroidal antiinflammatory agents.

The above-cited properties are demonstrable in vitro and in vivo tests using advantageously mammals, e.g. rats, mice, dogs, monkeys and isolated cells or enzyme preparations thereof. Said compounds can be applied in vitro in the form of solutions, e.g. aqueous solutions, and in vivo advantageously orally, topically or parenterally, e.g. intravenously. The dosage in vitro may range from about $10^{-5}$ to $10^{-9}$ molar concentrations. The dosage in vivo may range, depending on the route of administration, between about 1 and 100 mg/kg.

Cyclooxygenase inhibition is determined in vitro using cellular assays for inhibition of both cyclooxygenase-1 and cyclooxygenase-2.

The cellular assays for testing cyclooxygenase inhibitors are based on the fact that the cyclooxygenase enzyme (prostaglandin H synthase) catalyzes the rate limiting step in prostaglandin synthesis from arachidonic acid. Two enzymes mediate the reaction: COX-1 is a constitutive form of the enzyme whereas COX-2 is induced in response to various growth factors and cytokines. Cell lines have been established which express one form of the enzyme: a human skin fibroblast line which can be induced with IL-1 to synthesize COX-2, and the kidney epithelial cell line 293 which has been stably transfected to constitutively express COX-1. Both isoforms metabolize arachidonic acid into the stable metabolite prostaglandin $E_2$. Arachidonic acid can be added exogenously to increase output to easily measurable levels. The levels of prostaglandin $E_2$ in the extracellular medium are assayed by radioimmunoassay as a measure of enzyme activity. The relative activities of each isoform are compared to assess compound selectivity.

In vitro cyclooxygenase-1 (COX-1) and cyclooxygenase-2 (COX-2) inhibition is determined in the cell-based assays in order to assess the in vitro activity and selectivity for COX-2 inhibition, using a prostaglandin $E_2$ radioimmunoassay. The cells utilized are primary human fibroblasts induced with interleukin-1 to produce COX-2, and the human kidney epithelial cell line 293 stably transfected to produce COX-1 constitutively. Cells are plated out into well plates in which the assay is performed. Fibroblasts are stimulated to synthesize COX-2 by treatment overnight with IL-1; the 293 cells require no induction. Both cell lines are pre-treated with compound dilutions for 15 minutes at 37° C., then 40 $\mu$M arachidonic acid is added as exogenous substrate for the production of $PGE_2$, which is measured in supernatant by radioimmunoassay. For $IC_{50}$ determinations, compounds are tested at 5 concentrations in quadruplicate (highest concentration 30 $\mu$M); the mean inhibition of $PGE_2$ (compared to cells not treated with compound) for each concentration is calculated, a plot made of mean % inhibition vs. log compound concentration for all experiments, and the overall $IC_{50}$ value calculated using a 4-parameter logistic fit.

$IC_{50}$ values for compounds of formula I in the COX-2 inhibition assay are as low as about 0.005 $\mu$M whereas $IC_{50}$ values in the COX-1 inhibition assay are greater than 30 $\mu$M.

Illustrative of the invention, the compounds of examples 1(d), 1(g) and 3(a) have an $IC_{50}$ of about 0.13, 0.25, 0.007 $\mu$M, respectively, for COX-2 inhibition with no significant COX-1 inhibition at 30 $\mu$M.

The inhibition of prostaglandin-$E_2$ production produced by COX-2 can be determined in vivo in the lipopolysaccharide (LPS)-challenged subcutaneous air pouch model in the rat (see "Advances in Inflammation Research", Raven Press, 1986 and J. Med. Chem. 39, 1846 (1996)).

Female Lewis rats are anesthetized and then dorsal air pouches are prepared by subcutaneous injection of 10 ml of air through a sterile 0.45 micron syringe-adapted filter. Twenty-four hours after preparation, the air pouches are injected with LPS (8 $\mu$g/pouch) suspended in sterile phosphate buffered saline. Compounds for evaluation are suspended in fortified cornstarch and administered by gavage one hour prior to LPS challenge. The pouch contents are harvested three hours after LPS challenge and $PGE_2$ levels present in the pouch fluids are measured by enzyme immunoassay. $ED_{50}$ values for inhibition of $PGE_2$ formation are calculated by least squares linear regression. Illustrative of the invention, the compounds of examples 1(d), 1(g), 3(a) and 6(a) have an $ED_{50}$ in the range of about 0.2 mg/kg p.o. to about 0.6 mg/kg p.o.

The in vivo inhibition of thromboxane $B_2$ ($TXB_2$) produced by COX-1 can be measured ex vivo in the serum of rats after oral administration of compound.

Briefly, rats are fasted overnight, administered compound in fortified cornstarch vehicle by gavage, and sacrificed by carbon dioxide inhalation 30 minutes to eight hours later. Blood is collected by cardiac puncture into tubes without anti-coagulant, allowed to clot and serum is separated by centrifugation. Serum is stored frozen for later analysis of thromboxane $B_2$ by radioimmunoassay. Each experiment contains the following groups (5–6 rats per group): vehicle control and test compounds, either at different doses or different time points. Thromboxane $B_2$ data is expressed as a percentage of the levels measured in the vehicle control group.

Illustrative of the invention, the compounds of examples 1(d), 1(g), 3(a), and 6(a) cause less than a 50% inhibition of serum thromboxane $B_2$ production at an oral dose which is 50–150 times the $ED_{50}$ value for in vivo COX-2 inhibition.

Antiinflammatory activity is determined using the carrageenan induced rat paw edema assay.

Sprague Dawley rats (200–225 g) are fasted overnight, then orally dosed with the compound suspended in a fortified cornstarch solution. After one hour, a 0.1 ml volume of 1% carrageenan in saline is injected into the subplantar region of the left hind paw which causes an inflammatory response. At 3 hours post carrageenan, the rats are euthanatized and both hind paws are cut off at the paw hair line and weighed on an electronic balance. The amount of edema in the inflamed paw is determined by subtracting the weight of the non-inflamed paw (right) from the weight of the inflamed paw (left). The percent inhibition by the compound is determined for each animal as the percent paw weight gained as compared to the control average. $ED_{30}$ values are determined for each dose-response using the curve fitting formula, $$100/1+(\text{Drug Concentration}/ED_{30})^{slope}$$

Mean $ED_{30}$ values are calculated as the average of $ED_{30}$ values determined from independent dose response assays.

Illustrative of the invention, the compounds of examples 1(d), 1(g), 3(a) and 6(a) inhibit carrageenan-induced edema with an $ED_{30}$ in the range of about 0.14 mg/kg p.o. to about 1.65 mg/kg p.o.

The gastric tolerability assay is used to assess gross ulceration in the rat, measured four hours after oral administration of the test compound. The test is carried out as follows: Rats are fasted overnight, administered compound in fortified cornstarch vehicle by gavage, and sacrificed by carbon dioxide inhalation four hours later. The stomachs are removed and gross gastric lesions counted and measured to give the total lesion length per rat. Each experiment contains the following groups (5–6 rats per group): vehicle control, test compounds, and diclofenac as a reference compound.

Data are calculated as the mean number of ulcers in a group, the mean length of ulcers (mm) in the group and as the ulcer index (UI).

UI=mean length of ulcers in a group×ulcer incidence where ulcer incidence is the fraction of animals in the group with lesions (100% incidence is 1).

Illustrative of the invention, the compounds of examples 1(d), 1(g), 3(a) and 6(a) are essentially free of any gastric ulcerogenic effect at 100 mg/kg p.o.

Intestinal tolerability can be determined by measuring the effect on intestinal permeability. Lack of increase in permeability is indicative of intestinal tolerability.

The method used is a modification of a procedure by Davies, et al., Pharm. Res. 1994; 11:1652-1656 and is based on the fact that excretion of orally administered $^{51}$Cr-EDTA, a marker of small intestinal permeability, is increased by NSAIDs. Groups of rats ($\geq$12/group) are administered a single, oral dose of test compound or vehicle by gastric intubation. Immediately following compound dose, each rat is administered $^{51}$Cr-EDTA (5 $\mu$Ci/rat) by gastric intubation. The rats are placed in individual metabolic cages and given food and water ad libitum. Urine is collected over a 24 hour period. Twenty-four hours after administration of $^{51}$Cr-EDTA the rats are sacrificed. To quantify compound effect on intestinal permeability, the excreted $^{51}$Cr-EDTA measured in the urine of compound treated rats is compared to the excreted $^{51}$Cr-EDTA measured in the urine of vehicle treated rats. Relative permeability is determined by calculating the activity present in each urine sample as a percent of the administered dose after correcting for background radiation.

Illustrative of the invention, the compounds of examples 1(d), 1(g), 3(a) and 6(a) demonstrate no effect or only a minimal effect on intestinal permeability at a dose of 30 mg/kg p.o.

The analgesic activity of the compounds of the invention is determined using the well-known Randall-Selitto assay.

The Randall-Selitto paw pressure assay measures antinociception (analgesic activity) in inflamed tissue by comparing the pressure threshold in the inflamed paw of the rat after oral administration of test drug with that in the inflamed paw of rats administered corn starch vehicle orally.

Groups of 10 male Wistar rats weighing 40–50 gms are fasted overnight prior to testing. Hyperalgesia is induced by the injection of 0.1 ml of a 20% suspension of Brewer's yeast with a 26 gauge needle into the subplantar region of the right hindpaw. The left paw is not injected and is used as the control paw for determination of hyperalgesia. Vehicle (Fortified corn starch suspension 3%) at 10 ml/kg, reference compound (diclofenac is run in every experiment at the same dose as test compounds) and test compounds at different doses suspended in vehicle at 1 ml/kg are administered orally 2 hours after the yeast injection. The threshold for paw withdrawal is quantified with a Basile Analgesymeter 1 hour after oral administration of test compounds. The nociceptive threshold is defined as the force in grams at which the rat withdraws its foot or vocalizes. Either vocalization or foot withdrawal is recorded as a response.

The data are analyzed by comparing the mean pain threshold of the corn starch vehicle-treated group for the inflamed and non-inflamed paws to that of individual drug-treated rats. Individual rats in the drug-treated groups and positive control (diclofenac) group are called reactors if the individual pain threshold in each paw exceeds the control group mean threshold by two standard deviations of that mean. The mean pain thresholds of the inflamed paw in the control group are compared to the individual pain thresholds of the inflamed paw in the test drug group. The non-inflamed control mean pressure threshold is compared to the non-inflamed individual pressure thresholds in the test groups. Results are expressed as number of reactors in each test group (n =10) for inflamed and non-inflamed paws. Percentages are calculated by dividing number of reactors by total number of rats used for a compound.

Illustrative of the invention, the compounds of examples 1(d), 1(g), 3(a) and 6(a) all increase the pain threshold in the inflamed paw at 10 mg/kg administered orally. These compounds selectively elevate the pain threshold in the inflamed paw with no threshold elevation in the non-inflamed paw indicating a peripheral mechanism.

The antiarthritic effect of the compounds of the invention can be determined in the well-known chronic adjuvant arthritis test in the rat.

Ocular effects can be demonstrated in well-known ophthalmic assay methods. Similarly antitumor activity can be demonstrated in well-known antitumor animal tests.

The compounds of formula I can be prepared e.g.

(a) by coupling a compound of formula II or IIa

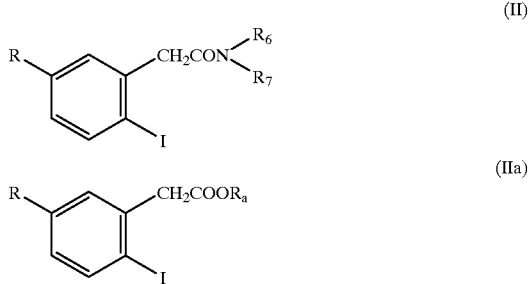

wherein R has meaning as defined above; $R_a$ is lower alkyl, preferably isopropyl; and $R_6$ and $R_7$ represent lower alkyl; or $R_6$ and $R_7$ together with the nitrogen atom represent piperidino, pyrrolidino or morpholino;

with a compound of formula III

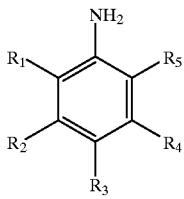
(III)

wherein $R_1$, $R_2$, $R_3$, $R_4$ and $R_5$ have meaning as defined above in the presence of copper and cuprous iodide to obtain a compound of formula IV or IVa

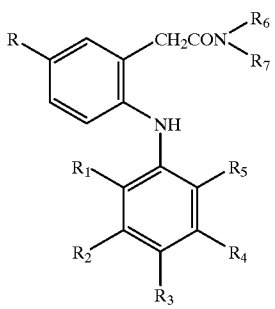
(IV)

(IVa)

and hydrolyzing the resulting compound of formula IV or IVa to a compound of formula I; or (b) for compounds in which R represents ethyl, by condensing a compound of formula V

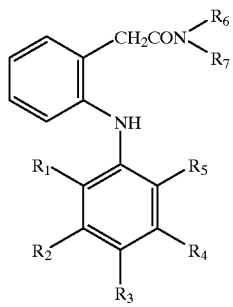
(V)

wherein $R_1$–$R_7$ have meaning as defined herein, with a reactive functional derivative of acetic acid, such as acetyl chloride, in a Friedel-Crafts acylation to reaction to obtain a compound of the formula VI

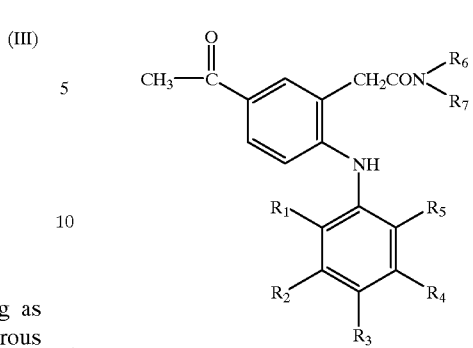
(VI)

wherein $R_1$–$R_7$ have meaning as defined herein which is in turn hydrogenolyzed and then hydrolyzed to obtain a compound of formula I wherein R represents ethyl; or (c) by hydrolyzing a lactam of formula VII

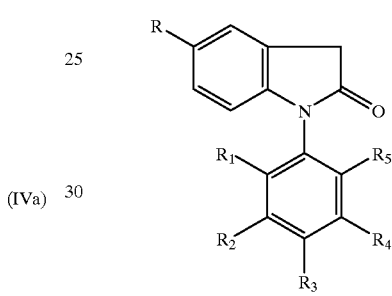
(VII)

wherein R and $R_1$–$R_5$ have meaning as defined herein, with a strong base; and in above processes, if desired, temporarily protecting any interfering reactive groups and then isolating the resulting compound of the invention; and, if desired, converting any resulting compound into another compound of the invention; and/or if desired converting a free carboxylic acid of the invention into a pharmaceutically acceptable ester derivative thereof; and/or if desired, converting a resulting free acid into a salt or a resulting salt into the free acid or into another salt.

In starting compounds and intermediates, which are converted to the compounds of the invention in a manner described herein, functional groups present such as amino, hydroxy and carboxyl groups, are optionally protected by conventional protecting groups that are common in preparative organic chemistry. Protected hydroxy, amino and carboxyl groups are those that can be converted under mild conditions into free amino, hydroxy and carboxyl groups without other undesirable side reactions taking place. For example, hydroxy protecting groups are preferably benzyl or substituted benzyl groups, or acyl groups such as pivaloyl.

The preparation of compounds of formula IV according to process (a) is carried out under conditions of a modified Ullmann condensation for the preparation of diarylamines, e.g. in the presence of copper powder and copper (I) iodide and potassium carbonate, in an inert high boiling solvent such as nitrobenzene, toluene, xylene or N-methylpyrrolidone, at elevated temperature, e.g. in the range of 100°–200° C., preferably at reflux temperature, according to general methodology described by F. Nohara, Chem. Abstr. 94, 15402x (1951) and Moser et al., J. Med. Chem. 33, 2358 (1990).

Intermediates of Formula IV wherein $R_1$, or $R_5$ is methyl or ethyl can be prepared from intermediates of formula IV, wherein $R_1$, or $R_5$ is bromo by reaction with tetramethyltin or tetraethyltin under conditions of a Heck reaction, that is in the presence of a palladium salt (such as $Pd(OAc)_2$ or $PdCl_2$), a triarylphosphine (such as tri (o-tolyl)phosphine) and a base (such as triethylamine, sodium acetate) in a polar solvent such as dimethylformamide.

Hydrolysis of the resulting ortho-anilinophenylacetamides of formula IV is carried out in aqueous alkali hydroxide, e.g. in 6N NaOH in the presence of an alcohol (e.g. ethanol, propanol, butanol) at elevated temperature, such as reflux temperature of the reaction mixture.

The hydrolysis of esters of formula IVa is carried out according to methods known in the art, e.g. under basic conditions as described above for the compounds of formula IV or alternatively under acidic conditions, e.g. using methanesulfonic acid.

The starting materials of formula 11 or Ha are generally known or can be prepared using methodology known in the art, e.g. as described by F. Nohara in Japanese patent application No. 78/96,434 (1978).

For example, 5-methyl or 5-ethylanthranilic acid is converted to the ortho-diazonium derivatives followed by treatment with an alkali metal iodide in acid (e.g. sulfonic acid) to obtain 5-alkyl-2-iodobenzoic acid. Reduction to the corresponding benzyl alcohol (e.g. with diborane), conversion of the alcohol first to the bromide and then to the nitrile, hydrolysis of the nitrile to the acetic acid and conversion to the N,N dialkylamide according to methodology known in the art yields a starting material of formula II.

Alternatively, the starting materials of formula II wherein R is ethyl can be prepared by Friedel-Crafts acetylation of oxindole with e.g. acetyl chloride in the presence of aluminum chloride, reduction of the resulting ketone by e.g. catalytic hydrogenolysis, followed by hydrolytic cleavage of the resulting 5-ethyloxindole to 5-ethyl-2-aminophenylacetic acid. Diazotization in the presence of e.g. potassium iodide yields 5-ethyl-2-iodo-phenylacetic acid which is converted to an amide of formula II. Esters of formula Ila are prepared from the corresponding acids according to esterification methods known in the art.

The anilines of formula III are either known in the art or are prepared according to methods well-known in the art or as illustrated herein.

The preparation of 5-ethyl substituted compounds according to process (b) is carried out under conditions of Friedel-Crafts acylation e.g. in the presence of aluminum chloride in an inert solvent such as 1,2-dichloroethane, followed by hydrogenolysis, e.g. using palladium on charcoal catalyst, preferably in acetic acid as solvent, at room temperature and about 3 atmospheres pressure.

The starting materials of formula V are prepared generally as described under process (a) but starting with an amide of formula II in which R represents hydrogen, e.g. as described in J. Med. Chem. 33, 2358 (1990).

The preparation of the compounds of the invention according to process (c) can be carried out under conditions known in the art for the hydrolytic cleavage of lactams, preferably with a strong aqueous base, such as aqueous sodium hydroxide, optionally in the presence of an organic water miscible solvent such as methanol at elevated temperature in the range of about 50–100° C., as generally described in U.S. Pat. No. 3,558,690.

The oxindole starting materials are prepared by N-acylation of a diarylamine of the formula VII

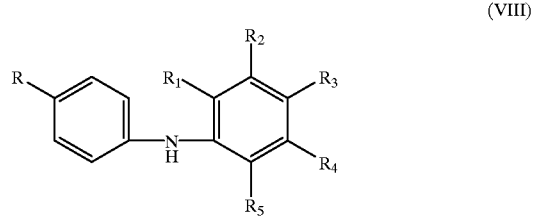

(VIII)

wherein R and $R_1$–$R_5$ have meaning as defined above with a haloacetyl chloride, preferably chloroacetyl chloride, advantageously at elevated temperature, e.g. near 100° C., to obtain a compound of the formula IX

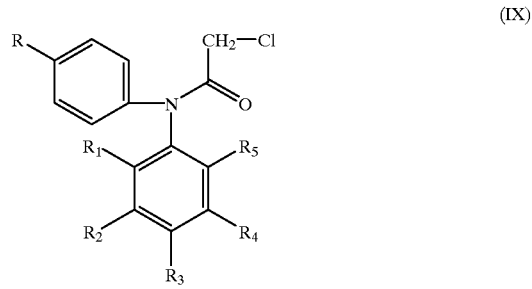

(IX)

wherein R and $R_1$–$R_5$ have meaning as defined hereinabove. Cyclization of a compound of formula IX is carried out under conditions of Friedel-Crafts alkylation in an inert solvent, such as dichlorobenzene, in the presence of Friedel-Crafts catalysts, e.g. aluminum chloride and ethylaluminum dichloride, at elevated temperature, e.g. at 120–175° C.

The diarylamines of formula VIII can be prepared by an Ullmann condensation and other methods known in the art, e.g. a Buchwald coupling reaction.

For example, the diarylamines of formula VIII wherein $R_1$, $R_2$, $R_4$ and $R_5$ are fluoro and $R_3$ is hydrogen can be prepared by reacting the corresponding aniline (4-ethyl- or 4-methyl-aniline) with pentafluorobenzene in the presence of a strong base such as lithium amide or n-butyllithium, as generally described in J. of Fluorine Chemistry 5, 323 (1975).

Esters of the carboxylic acids of formula I are prepared by condensation of the carboxylic acid, in the form of a salt or in the presence of a base, with a halide (bromide or chloride) corresponding to the esterifying alcohol (such as benzyl chloroacetate) according to methodology well known in the art, e.g. in a polar solvent such as dimethyl formamide, and if required further modifying the resulting product.

For example, if the esterification product is itself an ester, such can be converted to the carboxylic acid, e.g. by hydrogenolysis of a resulting benzyl ester. Also if the esterification product is itself a halide, such can for instance be converted to the nitrooxy derivative by reaction with e.g. silver nitrate.

For example, the compounds of formula Ia are preferably prepared by condensing a salt of a carboxylic acid of formula I above with a compound of formula

wherein X is a leaving group and $R_a$ is a carboxy protecting group to obtain a compound of formula Ia in carboxy protected form, and subsequently removing the protecting group $R_a$.

The esterification can be carried under esterification conditions known in the art, e.g. in a polar solvent such as dimethylformamide, at a temperature range of room temperature to about 100° C., preferably at a range of 40–60° C.

The salt of the acid of formula I is preferably an alkali metal salt, e.g. the sodium salt which may be prepared in situ.

Leaving group X is preferably halo, e.g. chloro or bromo, or lower alkylsulfonyloxy, e.g. methanesulfonyloxy.

Carboxy protecting group $R_a$ is preferably benzyl.

The resulting benzyl esters can be converted to the free acids of formula Ia preferably by hydrogenolysis with hydrogen in the presence of e.g. Pd/C catalyst in acetic acid at atmospheric pressure or under Parr hydrogenation at a temperature ranging from room temperature to about 50° C.

The invention includes any novel starting materials and processes for their manufacture.

Finally, compounds of the invention are either obtained in the free form, or as a salt thereof if salt forming groups are present.

The acidic compounds of the invention may be converted into metal salts with pharmaceutically acceptable bases, e.g. an aqueous alkali metal hydroxide, advantageously in the presence of an ethereal or alcoholic solvent, such as a lower alkanol. Resulting salts may be converted into the free compounds by treatment with acids. These or other salts can also be used for purification of the compounds obtained. Ammonium salts are obtained by reaction with the appropriate amine, e.g. diethylamine, and the like.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal, topical, and parenteral administration to mammals, including man, to inhibit COX-2-activity, and for the treatment of COX-2 dependent disorders, and comprise an effective amount of a pharmacologically active compound of the invention, alone or in combination, with one or more pharmaceutically acceptable carriers.

More particularly, the pharmaceutical compositions comprise an effective cyclooxygenase-2 inhibiting amount of a selective cyclooxygenase-2 inhibiting compound of the invention which is substantially free of cyclooxygenase-1 inhibiting activity and of side effects attributed thereto.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g. to the skin and eyes, include aqueous solutions, suspensions, ointments, creams, gels or sprayable formulations, for example, for delivery by aerosol or the like. Such topical delivery systems will in particular be appropriate for dermal application, e.g. for the treatment of skin cancer, for example, for prophylactic use in sun creams, lotions, sprays and the like. In this regard it is noted that compounds of the present invention are capable of absorbing UV rays in the range of 290–320 nm while allowing passage of tanning rays at higher wavelengths. They are thus particularly suited for use in topical, including cosmetic, formulations well-known in the art. Such may contain solubilizers, stabilizers, tonicity enhancing agents, buffers and preservatives. Formulations suitable for topical application can be prepared e.g. as described in U.S. Pat. No. 4,784,808. Formulations for ocular administration can be prepared e.g. as described in U.S. Pat. Nos. 4,829,088 and 4,960,799.

The pharmaceutical formulations contain an effective COX-2 inhibiting amount of a compound of the invention as defined above, either alone or in combination with another therapeutic agent.

For example, suitable additional active agents for use in relation to the treatment of neoplasia include e.g. any of the anti-neoplastic agents or radioprotective agents recited in International patent application WO 98/16227.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg, of the active ingredient.

The present invention also relates to methods of using the compounds of the invention and their pharmaceutically acceptable salts, or pharmaceutical compositions thereof, in mammals for inhibiting COX-2 and for the treatment of COX-2 dependent conditions as described herein, e.g. inflammation, pain, rheumatoid arthritis, osteoarthritis, ocular inflammatory disorders, glaucoma and dry eye disease.

Particularly the present invention relates to a method of selectively inhibiting cyclooxygenase-2 activity in a mammal without substantially inhibiting cyloxygenase-1 activity which comprises administering to a mammal in need thereof an effective cyclooxygenase-2 inhibiting amount of a compound of the invention.

Thus the present invention also relates to a method of treating cyclooxygenase-2 dependent disorders in mammals, which comprises administering to a mammal in need thereof an effective cyclooxygenase-2 inhibiting amount of a compound of the invention.

More particularly the present invention relates to a method of treating cyclooxygenase-2 dependent disorders in mammals while substantially eliminating undesirable side effects associated with cyclooxygenase-1 inhibiting activity which comprises administering to a mammal in need thereof an effective cyclooxygenase-2 inhibiting amount of a selective cyclooxygenase-2 inhibiting compound of the invention which is substantially free of cyclooxygenase-1 inhibiting activity.

More specifically such relates to a method of e.g. treating rheumatoid arthritis, osteoarthritis, pain or inflammation in mammals without causing undesirable gastrointestinal ulceration, which method comprises administering to a mammal in need thereof a correspondingly effective amount of a compound of the invention.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLE 1

(a) N,N-dimethyl-5-methyl-2-(2',4'-dichloro-6'-methylanilino)phenylacetamide (1.5 g, 4.3 mmol) is hydrolyzed with 6N NaOH (70 ml) as a two phase solution with n-BuOH (40 ml) at reflux temperature for 14 hours. After cooling to room temperature, the mixture is poured over ice (100 ml). Toluene (100 ml) is added and the mixture transferred to a separatory funnel. The aqueous phase is brought to a pH of 1 with 3 N HCl. The organic phase is separated and the aqueous phase re-extracted with toluene (100 ml). The combined organic solution is dried ($MgSO_4$) and concentrated under high vacuum (35–50 mbar), on a rotovap, taking care not to warm above 50°. Upon crystallization from $Et_2O$/hexane, 5-methyl-2-(2',4'-dichloro-6'-methylanilino)phenylacetic acid is obtained as a tan solid, m.p. 137–141°.

The starting material, N,N-dimethyl-5-methyl-2-(2',4'-dichloro-6'-methylanilino)phenylacetamide is prepared in the following manner:

5-Methyl-2-iodobenzoic acid (100 g, 0.38 mol) is dissolved in THF (350 ml) and cooled in an ice bath. Borane-THF complex (380 ml of 1M in THF, 0.38 mol) is added dropwise. After addition is complete, the reaction is warmed to room temperature and stirred for 14 hours. The mixture is transferred to a large erienmeyer flask, cooled in an ice bath, and carefully quenched with water (250 ml). Evaporation of the THF on a rotovap gives a white suspension which is treated with additional water (1 L) and then filtered and dried in a vacuum dessicator over $P_2O_5$ to give 2-iodo-5-methylbenzyl alcohol as a white solid, m.p. 82–85°.

The benzylic alcohol (99.8 g, 0.38 mol) is dissolved in 48% HBr (500 ml) and heated to reflux temperature for 4 hours. The resulting benzylic bromide is isolated as a yellow solid by pouring the cooled mixture into a large volume (1.5 L) of water followed by filtration. The benzylic bromide (caution: lachrymator) is dissolved in EtOH (400 ml) and stirred at room temperature. Sodium cyanide (56 g, 1.14 mol) is dissolved in a minimum amount (~100 ml) of water and then added to the ethanolic solution of the benzylic bromide. The reaction is heated to reflux temperature for 3 hours and then cooled to room temperature. Ethanol is removed on a rotovap and the residue washed with a large volume (1 L) of water. The resulting 2'-iodo-5'-methylphenylacetonitrile is isolated as a white solid, m.p. 77–790°, by filtration.

The nitrile (94.5 g, 0.37 mol) is dissolved in EtOH (350 ml) and treated with NaOH (29.4 g, 0.74 mol) which has been dissolved in water (200 ml). The reaction is heated to reflux temperature for 14 hours. After cooling to room temperature, ethanol is removed on a rotovap and 6N HCl added until the pH=1. The solid 5-methyl-2-iodophenylacetic acid is filtered off and washed with water (2×500 ml). After drying over $P_2O_5$ in a vacuum dessicator, the solid 5-methyl-2-iodophenyl acetic acid (mp 112–114°, 83 g, 0.30 mol) is dissolved in $CH_2Cl_2$ (450 ml) that contains several drops of DMF. To the solution thionyl chloride (32 ml, 0.450 mol) is added and the reaction heated to reflux temperature overnight. After cooling to room temperature, the reaction mixture is diluted with additional $CH_2Cl_2$ (500 ml) and washed with water (2×250 ml), saturated $NaHCO_3$ (250 ml) and brine (250 ml). The solution is dried ($MgSO_4$) and concentrated on a rotovap to give 5-methyl-2-iodophenylacetyl chloride as a yellowish oil.

Dimethylamine (200 ml of 2 M solution in THF) is added dropwise to a solution of 5-methyl-2-iodophenylacetyl chloride in $Et_2O$ (500 ml) which is cooled in an ice bath. After the addition is complete, EtOAc (350 ml) is added and the solution is washed with water (350 ml), brine (250 ml) and dried ($MgSO_4$). Evaporation on a rotovap and trituration with 1:1 $Et_2O$/hexanes gives N,N-dimethyl-5-methyl-2-iodophenylacetamide as a light tan solid, m.p. 47–49°.

N,N-Dimethyl-5-methyl-2-iodophenylacetamide (3.5 g, 11.5 mmol) and 2,4-dichloro-6-methylaniline (4.1 g, 23 mmol) are stirred in xylenes (100 ml) with copper powder (0.18 g, 2.9 mmol), copper(I) iodide (0.55 g, 2.9 mmol) and anhydrous potassium carbonate (1.6 g, 11.5 mmol). The reaction is heated to reflux temperature for 48 hours. While still slightly warm (40°) the brown suspension is filtered through a pad of Celite, which in turn is rinsed with toluene (75 ml). The filtrate is evaporated on a rotovap and flash chromatographed on silica gel ($R_f$ 0.30 in 40% EtOAc/hexane) to give N,N-dimethyl-5-methyl-2-(2',4'-dichloro-6'-methylanilino) phenylacetamide as an off-white crystalline solid, m.p. 119–124°.

Similarly prepared are:
(b) 5-methyl-2-(2',3',5',6'-tetrafluoroanilino)phenylacetic acid, m.p. 153–156°;
(c) 5-methyl-2-(2',6'-dichloroanilino)phenylacetic acid, m.p.168–170°;
potassium salt, m.p. 318–320°; sodium salt, m.p. >300°;
(d) 5-methyl-2-(2'-chloro-6'-fluoroanilino)phenylacetic acid, m.p. 158–159°;
(e) 5-methyl-2-(2',6'-dichloro-4'-methylanilino) phenylacetic acid, m.p. 179–182°;
(f) 5-methyl-2-(2'-chloro-6'-methylanilino)phenylacetic acid, m.p. 138–140°;
(g) 5-methyl-2-(2',4'-difluoro-6'-chloroanilino) phenylacetic acid, m.p. 157–159°;
(h) 5-methyl-2-(2'-fluoro-4',6'-dichloroanilino) phenylacetic acid, m.p. 178–180°;
(i) 5-methyl-2-(2'-chloro-4'-fluoro-6'-methylanilino) phenylacetic acid, m.p. 154–156°.
(j) 5-methyl-2-(2'-chloro-4'-hydroxy-6'-fluoroanilino) phenylacetic acid, m.p. 180–182°.

The starting material for compound of Example 1(j), 2-chloro-4-pivaloyloxy-6-fluoroaniline, is prepared in the following manner:

To a mixture of 7.0 g (0.045 mol) of 3-fluoro-4-nitrophenol and 6.7 g (0.067 mol) of triethylamine in 20 ml of methylene chloride cooled to 0° is added 6.5 g (0.054 mol) of pivaloyl chloride in a dropwise manner. The reaction is allowed to warm to room temperature and stirred overnight. The reaction is quenched with water and extracted with ethyl acetate. The organic layer is washed successively with 1 N hydrochloric acid, saturated aqueous sodium bicarbonate, and saturated brine, and then dried over magnesium sulfate. Filtration and removal of the solvents gives crude 2-fluoro-4-pivaloyloxy-nitrobenzene which is dissolved in 200 ml of absolute ethanol. To the solution is added 0.9 g of 5% palladium on carbon, and the mixture is then hydrogenated under 30 psi hydrogen for two hours. The catalyst is filtered and the solvent removed to give 2-fluoro-4-pivaloyloxyaniline.

A mixture of 7.3 g (0.035 mol) of 2-fluoro-4-pivaloyloxyaniline and 5.1 g (0.038 mol) of N-chlorosuccinimide in 50 ml of fluorobenzene is heated to reflux under a nitrogen atmosphere for two hours. After cooling to room temperature, the solvent is removed, water is added, and the mixture is extracted with ethyl acetate. The organic layer is washed with 1 N sodium hydroxide, and saturated brine, and dried over magnesium sulfate. Filtration and removal of the solvents gives a residue which is purified by silica gel chromatography (20% ethyl acetate/hexane) to give 2-chloro-4-pivaloyloxy-6-fluoroaniline. Conversion of 2-chloro-4-pivaloyloxy-6-fluoroaniline to 5-methyl-2-(2'-chloro-4'-hydroxy-6'-fluoroanilino)phenylacetic acid is carried out in a manner similar to that described in Example 1, the pivaloyl group being hydrolyzed in the last step along with the dimethylamide to give the final product.

EXAMPLE 2

Similarly prepared according to procedures described in Example 1 are:
(a) 5-ethyl-2-(2'-fluoro-6'-chloroanilino)phenylacetic acid, m.p. 147–148°;

The starting material, 5-ethyl-2-iodo-N,N-dimethylphenylacetamide is prepared as follows:

$AlCl_3$ (303 g, 2.27 mol) is placed in a 3-necked flask fitted with a thermometer and a dropping funnel. While stirring DMF (50 ml) is added dropwise and the temperature rises to about 60°. The mixture is cooled down to 45°, and oxindole (33 g, 0.25 mol) is added in 3 portions. After an additional 10 minutes, acetyl chloride (36 ml, 0.5 mol) is added. The mixture is stirred for an additional 30 minutes at room temperature. The mixture is poured onto ice (3000 g). This results in the formation of a solid which is filtered off, washed first with water and then with cold methanol (1000 ml), and then dried to give 5-acetyloxindole.

The 5-acetyloxindole (54 g, 308 mmol), acetic acid (400 ml) and palladium on carbon (10%, 5 g) are combined and treated with hydrogen for 14 hours at 55 psi. The catalyst is removed by filtering through a bed of Celite, the filtrate is concentrated under reduced pressure and the residue is treated with ether to give 5-ethyloxindole 5-Ethyloxindole (~54 g, ~335 mmol), ethanol (750 ml), water (150 ml) and potassium hydroxide (65 g, 1.62 mol) are combined and heated at reflux for 3 days. The mixture is allowed to cool and then filtered through a bed of Celite. The filtrate is concentrated under reduced pressure, water is added and the pH adjusted to 6.5. The precipitate is filtered off, washed with water and dried in an oven overnight to yield 5-ethyl-2-aminophenylacetic acid.

A mixture of water (405 ml) and concentrated HCl (48 ml) is stirred and cooled to 0°. 5-Ethyl-2-aminophenylacetic acid (53.7 g, 300 mmol) is slowly added while maintaining the temperature at 0–2°. After this addition a solution of sodium nitrite (22.2 g, 322 mmol) in 60 ml water is added dropwise over 30 minutes keeping the temperature at 0–2°. After a further 20 minutes a solution of potassium iodide (48 g, 290 mmol) in 18 ml conc HCl and 130 ml water is added dropwise while keeping the temperature below 10° C. The reaction mixture is allowed to warm to room temperature and then heated to reflux for 2 hours. The mixture is extracted with ethyl acetate and ether (1:1 mixture, 4×300 ml), the organic layer is then washed first with a 30% aqueous solution of sodium thiosulfite and then with a sodium hydroxide solution (0.1 M) before being acidified to pH 6 and extracted with ethyl acetate. This solution is washed with saturated brine, dried (magnesium sulfate), filtered, and the solvent removed under reduced pressure. The residue is treated with hexane to yield 5-ethyl-2-iodophenylacetic acid.

5-Ethyl-2-iodophenylacetic acid is dissolved in methylene chloride (400 ml) and DMF (1 ml) is added. Thionyl chloride (21 ml, 300 mmol) is then added dropwise over 20 minutes. The mixture is heated to reflux and heating continued for 3.5 hours when the mixture is cooled and ice-water (400 ml) and methylene chloride (300 ml) are added. The layers are separated, the organic layer is washed with a sodium bicarbonate solution, saturated brine, dried (magnesium sulfate), and evaporated under reduced pressure to yield 5-ethyl-2-iodophenylacetyl chloride.

The acid chloride (46 g 150 mmol) is dissolved in ether (500 ml) and stirred at −35°. Dimethylamine (250 ml of 2M solution in THF, 500 mmol) is added dropwise at −35° and the mixture allowed to warm to room temperature and then stirred for 60 hours. Ethyl acetate and water are added and the layers separated. The organic layer is washed with saturated brine and the combined aqueous layers washed with ether. The combined organic layers are now dried (magnesium sulfate), and the solvent is removed under reduced pressure. Hexane is added to yield N,N-dimethyl 5-ethyl-2-iodophenylacetamide as a solid.

(b) 5-ethyl-2-(2'-chloro-6'-methylanilino)phenylacetic acid, m.p. 125–126°;

(c) 5-ethyl-2-(2',3',6'-trifluoroanilino)phenylacetic acid, m.p. 138–140°;

(d) 5-ethyl-2-(2',3',5',6'-tetrafluoro 4'-ethoxyanilino) phenylacetic acid, m.p. 131–132°;

(e) 5-ethyl-2-(2'-chloro-4',6'-difluoroanilino)phenylacetic acid, m.p. 160–162°;

(f) 5-ethyl-2-(2',4'-dichloro-6'-fluoroanilino)phenylacetic acid, m.p.169–171°.

EXAMPLE 3

(a) N,N-Dimethyl-5-ethyl-2-(2',3',5',6'-tetrafluoroanilino) phenylacetamide (26 g, 0.073 mol) and 6N NaOH (150 ml) are stirred as a two phase solution with n-BuOH (150 ml) at reflux temperature for 14 hours. After cooling to room temperature, the reaction is poured over ice (500 ml). Toluene (500 ml) is added and the mixture transferred to a separatory funnel. The aqueous phase is brought to a pH of 1 with 3 N HCl. The organic layer is separated and the aqueous phase re-extracted with toluene (250 ml). The combined organic layers are dried (MgSO$_4$) and concentrated under high vacuum (35–50 mbar) on a rotovap taking care not to warm above 500°. Small white needles are obtained by crystallization of the residue from hexane, m.p. 164–166°. Recrystallization from cyclohexane gives 5-ethyl-2-(2',3',5',6'-tetrafluoroanilino) phenylacetic acid a white solid, m.p. 165–169°.

The starting material N,N-dimethyl-5-ethyl-2-(2',3',5',6'-tetrafluoroanilino)phenylacetamide is prepared in the following manner N,N-Dimethyl-2-iodophenylacetamide (60 g, 0.208 mol), 2',3',5',6'-tetrafluoroaniline (100 g, 0.606 mol), copper powder (6.6 g, 0.104 mol), copper(I) iodide (19.8 g, 0.104 mol) and anhydrous potassium carbonate (28.7 g, 0.208 mol) are stirred together in 1000 ml of xylenes. The reaction is heated to reflux temperature for 48 hours. While still slightly warm (40°) the brown suspension is filtered through a pad of Celite which in turn is rinsed with toluene (250 ml). The filtrate is evaporated on a rotovap and then flash chromatographed on silica-gel (Rf 0.25 in 30% EtOAc/hexane). Crystallization from pentane/Et$_2$O gives N,N-dimethyl-2-(2',3',5',6'-tetrafluoroanilino)phenylacetamide, m.p. 109–110°.

Under an inert atmosphere, acetyl chloride (29.1 ml, 0.385 mol) is slowly added to a suspension of aluminum chloride (51.2 g, 0.385 mol) stirred in 1,2-dichloroethane (750 ml). After stirring at room temperature for 1 hour a yellow solution is obtained. The solution is cooled in an ice bath and N,N-dimethyl-2-(2',3',5',6'-tetrafluoroanilino) phenylacetamide (40 g, 0.123 mol) is added.

The reaction is allowed to warm to room temperature and then warmed to 800° for 0.5 hours. The reaction is poured over ice and extracted with EtOAc (2×750 ml). The organic extract is washed with water (750 ml), saturated NaHCO$_3$ solution (500 ml) and brine (500 ml). Evaporation on a rotovap and trituration with Et$_2$O gives N,N-dimethyl-5-acetyl-2-(2',3',5',6'-tetrafluoroanilino)phenylacetamide as a white solid, m.p. 112–114°.

N,N-dimethyl-5-acetyl-2-(2',3',5',6'-tetrafluoroanilino) phenylacetamide (30 g, 0.802 mol) is dissolved in HOAc (150 ml) and hydrogenated (55 psi) with a 10% Pd/C (1.5 g) catalyst for 8 hours. The catalyst is removed by filtration through Celite and the filtrate poured into water (500 ml) and EtOAc (500 ml). The organic layer is washed with water (750 ml), neutralized with saturated Na$_2$CO$_3$ solution (500 ml) and washed with brine (500 ml). Evaporation on a rotovap followed by trituration with hexanes gives N,N-dimethyl-5-ethyl-2-(2',3',5',6'-tetrafluoroanilino) phenylacetamide, m.p. 105–106°.

Similarly prepared are:

(b) 5-ethyl-2-(2',4'-dichloro-6'-methylanilino) phenylacetic acid, m.p. 180–183°;

(c) 5-ethyl-2-(2',6'-dichloroanilino)phenylacetic acid, m.p. 133–136°.

EXAMPLE 4

(a) N-(2,3,5,6-tetrafluorophenyl)-5-ethyloxindole (72.67 g; 0.235 mol, is slurried in water containing a little methanol (10% v/v; 253 ml), and sodium hydroxide solution (50 wt %; 16.1 ml) is added. The mixture is stirred at 80–85° for 2–4 hours, then cooled to ambient temperature. The reaction solution is partially concentrated under reduced pressure (25–30 mm). After removal of 50 ml of the solvent, the mixture is diluted with water (150 ml) and t-butyl methyl ether (250 ml). The cooled mixture is acidified to pH 6.5–7.0 with aqueous HCl (12.1 N; 19.5 ml), keeping the temperature at 0–5°. The aqueous layer is discarded and the organic layer is washed with water (250 ml). The organic layer is concentrated under reduced pressure (20–100 mm) while exchanging the solvent to toluene. After the more volatile components have been removed, the batch volume is adjusted to 400–450 ml. This mixture is warmed to 700°, clarified, concentrated to one-half volume, and cooled to 0° After stirring at this temperature for 2 hours, the product is collected and is washed with toluene/heptane (10:90; 100 ml). The resulting solid is dried under reduced pressure at 50–60° for 4–8 hours to give 5-ethyl-2-(2',3',5',6'-tetrafluoroanilino)phenylacetic acid of Example 3.

The starting material is prepared as follows: 4-Ethylaniline (242.36 g; 2.00 mol) is dissolved in dry tetrahydrofuran (900 ml). A solution of n-BuLi (2.5 M in hexanes, 800 ml; 2.00 mol) is added under $N_2$ with cooling maintaining the reaction temperature below 15°. After stirring for 1 hour at 10°, neat pentafluorobenzene (168.06 g; 1.00 mol) is added with cooling to the mixture, keeping the temperature at 10–200. The reaction is stirred at ambient temperature for 1.5 hours, then aqueous HCl (6 N; 500 ml) is added slowly with vigorous stirring and cooling, keeping the reaction temperature below 350°. The quenched reaction is stirred at ambient temperature for 0.5–18 hours. The aqueous layer is separated, and the organic phase is concentrated under reduced pressure (30–150 mm) to one-fourth volume. The concentrate is diluted with heptane (300 ml) and extracted with water (300 ml). The separated top organic layer is stirred over 230–400 mesh silica gel (50 g) and filtered. The filter cake is washed with heptane (4×50 ml). The combined filtrate and washings are concentrated under reduced pressure (20–30 mm) to give solid crude product. This material is recrystallized from hot heptane (200 ml) and collected at 0°. This solid is washed with cold heptane (100 ml) and dried under reduced pressure at 400 to give pure N-(2',3',5',6'-tetrafluorophenyl)4-ethylaniline.

The diphenylamine derivative (230.0 g; 0.854 mol; 1.0 eq) is treated with chloroacetyl chloride (192.96 g; 1.709 mol; 2.0 eq) at 100–115° for 2 hours (vigorous HCl evolution is controlled by rate of heating). The mixture is cooled to ambient temperature, then concentrated under reduced pressure (10–12 mm) to 80–90% of the original volume. 1,2-Dichlorobenzene (80 ml) is added and the diluted mixture is concentrated under reduced pressure (10–12 mm) until no more chloroacetyl chloride is found by GC analysis (30–40 ml distilled) to give crude N-(2',3',5',6'-tetrafluorophenyl)-N-chloroacetyl-4-ethylaniline in solution.

Anhydrous $AlC_3$ (170.84 g; 1.281 mol; 1.5 eq) was slurried with 1,2-dichlorobenzene (480 ml) under $N_2$ and cooled to 0°. The crude product solution from the previous step (theoretically containing 295.34 g; 0.854 mol; 1.0 eq) is added slowly with vigorous stirring, keeping the temperature below 60°. A solution of $EtAlCl_2$ (1.8M in toluene; 733 ml; 1.319 mol; 1.7 eq) is added, and the vigorously stirred reaction mixture is heated to ~160°, distilling toluene (135–160°) at ambient pressure. Upon cessation of the distillation (~690 ml), the reaction temperature is held at 155–165° for 3.5–5 hours. The mixture is cooled to ambient temperature, then poured onto crushed ice (2.5 kg) with vigorous stirring under $N_2$. The reaction vessel is rinsed with 1,2-dichlorobenzene (50 ml). The cold quenched product slurry is filtered and the filtercake is washed sequentially with 10% 1,2-dichlorobenzene/heptane (100 ml) and heptane (100 ml). The material is dried under reduced pressure at 80–90° for 12–16 hours to give N-(2',3',5',6'-tetrafluorophenyl)-5-ethyloxindole.

EXAMPLE 5

(a) N,N-Dimethyl 5-ethyl-2-(4'-chloro-2'-fluoro-6'-methylanilino)phenylacetamide is converted as in the previous examples to 5-ethyl-2-(4'-chloro-2'-fluoro-6'-methylanilino)phenylacetic acid, m.p. 153–156°.

The starting material is prepared as follows:

Ullmann condensation of N,N-dimethyl-5-ethyl-2-iodophenylacetamide with 2-bromo-4-chloro-6-fluoroaniline according to the procedure described in Example 1 yields N,N-dimethyl-5-ethyl-2-(2'-bromo-4'-chloro-6'-fluoroanilino)phenylacetamide.

N,N-Dimethyl-5-ethyl-2-(2'-bromo-4'-chloro-6'-fluoroanilino)phenylacetamide (2.5 g, 6.0 mmol) is combined with DMF (10 ml), triethylamine (10 ml), tri-o-tolylphosphine (0.5 g, 1.6 mmol), tetramethyltin (4 ml, 5.16g, 28.9 mmol) and palladium acetate (0.25 g, 1.1 mmol), and the mixture heated in a sealed tube for 3 days at 95°. The tube is allowed to cool and carefully opened. Water and ethyl acetate are added to the reaction and the mixture separated. The organic fraction is washed with a dilute NaCl solution (2×50 ml). The combined aqueous fractions are then washed with ethyl acetate and the combined organic fractions are then dried (magnesium sulfate). The material is absorbed onto a small amount of silica gel and purified by flash chromatography (on silica, ethyl acetate:hexanes, 1:4 to 1:1) to give N,N-dimethyl-5-ethyl-2-(4'-chloro-2'-fluoro-6'-methylanilino)phenylacetamide.

Similarly prepared are:
(b) 5-ethyl-2-(2',4'-difluoro-6'-methylanilino) phenylacetic acid, m.p. 143–145°;
(c) 5-ethyl-2-(2'-chloro-4'-fluoro-6'-methylanilino) phenylacetic acid, m.p. 151–154°;

EXAMPLE 6

(a) 5-Ethyl-2-(2',3',5',6'-tetrafluoroanilino)phenylacetic acid (1.0 g, 3.06 mmol) in THF (100 ml) is treated with 1 N sodium hydroxide (3.06 ml, 3.06 mmol) for 1 hour. The mixture is concentrated on a rotovap and then dried by evaporating first with THF (2×100 ml) and then with benzene (2×100 ml). The remaining off-white sodium salt of 5-ethyl-2',3',5',6'-tetrafluoroanilino)phenylacetic acid is dried under high vacuum overnight. Sodium 5-ethyl-2-(2', 3',5',6'-tetrafluoroanilino)phenylacetate (0.5 g, 1.43 mmol) and benzyl 2-bromoacetate (272 µl, 1.72 mmol) are stirred at 50° in dimethylformamide (50 ml) for 14 hours. The reaction mixture is cooled to room temperature and partitioned between EtOAc (200 ml) and water (200 ml). The organic layer is washed again with water (2×200 ml), brine (100 ml), dried (MgSO$_4$) and concentrated on a rotovap. The crude benzyl ester is flash chromatographed on silica (10–15% EtOAc/hexane) to provide the benzyloxycarbonylmethyl ester of 5-ethyl-2-(2',3',5',6'-tetrafluoroanilino) phenylacetic acid as a colorless oil. The oil is dissolved in HOAc (20 ml) and hydrogenated (55 psi) with a 10% Pd/C (0.1 g) catalyst for 1 hour. The catalyst is removed by filtration through Celite and the filtrate poured into water (200 ml) and EtOAc (200 ml). The organic layer is washed with water (250 ml) and brine (100 ml). Evaporation on a rotovap and trituration with Et$_2$O/hexanes gives the ester, carboxymethyl 5-ethyl-2-(2',3',5',6'-tetrafluoroanilino) phenylacetate, m.p. 151–153°, of the formula

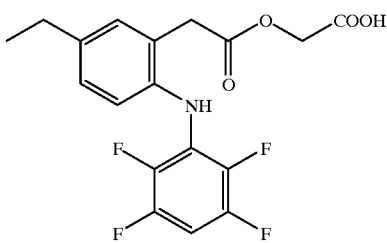

Similarly prepared are:
(b) carboxymethyl 5-ethyl-2-(2',4'-dichloro-6'-methylanilino)phenylacetate, m.p. 123–125°;
(c) carboxymethyl 5-ethyl-2-(2',6'-dichloroanilino) phenylacetate, m.p.124–126°;
(d) carboxymethyl 5-ethyl-2-(2',4'-difluoro-6'-chloroanilino)phenylacetate, m.p.142–144°;
(e) carboxymethyl 5-ethyl-2-(2',4'-dichloro-6'-fluoroanilino)phenylacetate, m.p. 132–134°;
(f) carboxymethyl 5-ethyl-2-(2'-chloro-6'-fluoroanilino) phenylacetate, m.p. 106–108°;
(g) carboxymethyl 5-methyl-2-(2'-fluoro-4',6'-dichloroanilino)phenylacetate, m.p. 148–150°;
(h) carboxymethyl 5-methyl-2-(2',6'-dichloroanilino) phenylacetate, m. p.125–126°;
(i) carboxymethyl 5-methyl-2-(2'-chloro-6'-fluoroanilino) phenylacetate, m.p. 96–98°.
(j) carboxymethyl 5-methyl-2-(2',4'-difuoro-6'-chloroanilino)phenylacetate.

EXAMPLE 7

5-Ethyl-2-(2',3',5',6'-tetrafluoroanilino)phenylacetic acid (1.0 g, 3.06 mmol) in THF (100 ml) is treated with 1 N sodium hydroxide (3.06 ml, 3.06 mmol) for 1 hour. The mixture is concentrated on a rotovap and the residue is then treated and evaporated to dryness first with THF (2×100 ml) and then with benzene (2×100 ml). The remaining off-white sodium salt of 5-ethyl-2-(2',3',5',6'-tetrafluoroanilino) phenylacetic acid is dried under high vacuum overnight.

The sodium 5-ethyl-2-(2',3',5',6'-tetrafluoroanilino) phenylacetate (2.0 g, 6.2 mmol) is dissolved in DMF (70 ml) and treated with 1-bromo- 4-chlorobutane (1.2 g, 6.9 mmol) at room temperature overnight. The reaction mixture is concentrated under high vacuum (35–50 mbar) on a rotovap. The resulting oil is partitioned between water (200 ml) and Et$_2$O (200 ml). The organic layer is washed with brine (100 ml), dried (MgSO$_4$) and concentrated on a rotovap to give the chlorobutyl ester as a light-brown oil. The chlorobutyl ester is dissolved in CH$_3$CN (100 ml) and treated with silver nitrate (8.7 g, 50 mmol) at reflux temperature for 18 hours. The reaction is cooled to room temperature and the solvent removed on a rotovap. The residue is partitioned between CH$_2$Cl$_2$ (200 ml) and water (200 ml). The organic layer is dried (MgSO$_4$), concentrated and flash-chromatographed (5% EtOAc/hexane) to give nitrooxybutyl 5-ethyl-2-(2',3', 5',6'-tetrafluoroanilino)phenylacetate as a clear oil.

EXAMPLE 8

Sodium 5-ethyl-2-(2',3',5',6'-tetrafluoroanilino) phenylacetate (7.3 g, 20.9 mmol) is dissolved DMF (100 ml) and treated with benzyl 2-methyl-2-bromopropionate (6.2 g, 24.2 mmol) at 500 for 96 hours. The reaction mixture is cooled to room temperature, and concentrated under high vacuum (35–50 mbar) on a rotovap. The resulting oil is partitioned between water (200 ml) and Et$_2$O (200 ml). The organic layer is washed with brine (100 ml), dried (MgSO$_4$) and concentrated on a rotovap to give a light-brown oil. Flash chromatography (0–10% EtOAc/hexane) on silica-gel gives the ester as a light-red oil. The ester (1.5 g, 3.0 mmol) is dissolved in EtOAc (150 ml) and hydrogenated (55 psi) with a 10% Pd/C (0.3 g) catalyst for 1 hour. The catalyst is removed by filtration through Celite (500 ml). Evaporation on a rotovap followed by trituration with hexanes gives 1-carboxy-1-methylethyl 5-ethyl-2-(2',3',5',6'-tetrafluoroanilino)phenylacetate as a crystalline white solid, m.p. 104–108°.

EXAMPLE 9

(a) Isopropyl 5-methyl-2-(2'-fluoro-6'-trifluoromethylanilino)phenylacetate (2.9 g, 8.4 mmol) is dissolved in methanesulfonic acid (25 ml) and stirred at room temperature for 8 hours. The reaction mixture is slowly added to 200 ml of ice in a beaker. After the ice has melted, the solution is stirred to produce a white solid which is isolated by filtration. The solid is flash chromatographed on silica-gel using 35% EtOAc as an eluant to give 5-methyl-2-(2'-fluoro-6'-trifluoromethylanilino) phenylacetic acid as a white solid, m.p. 155–156°.

The starting material is prepared as follows:

2-Iodo-5-methylphenylacetic acid (20.0 g, 72 mmol) and a catalytic amount of 98% sulfuric acid (0.2 ml) are dissolved in isopropyl alcohol (200 ml) and heated to reflux temperature for 48 hours. The solvent is removed on a rotovap and the residual oil partitioned between EtOAc (500 ml) and saturated NaHCO$_3$ solution (500 ml). The organic layer is separated, dried (MgSO$_4$) and concentrated on a rotovap. The residual oil is distilled using a kugelrohr apparatus to give a clear, colorless oil which solidifies on standing at room temperature to give isopropyl 2-iodo-5-methylphenylacetate, m.p. 48–50°.

Isopropyl 2-iodo-5-methylphenylacetate (10.0 g, 31 mmol), 2-amino-3-fluorobenzotrifluoride (20.0 g, 111 mmol), copper powder (1.1 g, 16 mmol), copper (I) iodide (3.1 g, 16 mmol) and K$_2$CO$_3$ (4.3 g, 31 mmol) are stirred together in xylenes (200 ml). The reaction mixture is heated to reflux temperature for 48 hours. While still slightly warm (400) the brown suspension is filtered through a pad of Celite, which in turn is rinsed with toluene (100 ml). The filtrate is evaporated on a rotovap and then flash chromatographed on silica-gel using 34% EtOAc in hexanes as the eluant. The product, isopropyl 5-methyl-2-(2'-fluoro-6'-trifluoromethylanilino)phenyl acetate, is isolated as a pale yellow oil.

(b) Similarily prepared is 5-methyl-2-(2',4'-dichloro-6'-trifluoromethylanilino)phenylacetic acid, m.p. 157–158°.

EXAMPLE 10

(a) To a degassed solution of 1500 ml of absolute ethanol and 510 ml of 2N NaOH (1.02 mol) is added 150 g (0.51 mol) of N-(2'-chloro-4',6'-difluorophenyl)-5-methyloxindole. The resultant mixture is degassed and heated to 60–65° for 2 hours. Most of the ethanol is removed under reduced pressure and then 4500 ml of water is added to the residue which is then washed three times with 1500 ml of toluene. The aqueous layer is cooled to 0° and adjusted to pH 6 using 1.2 N HCl. The solid is filtered off and washed with 100 ml of water and dried. Recrystallization from ethyl acetate and heptane gives 5-methy-2-(2',4'-difluoro-6'-chloroanilino)phenylacetic acid of Example 1(g).

The starting material is prepared in the following manner: 2-Bromo-4,6-difluoroaniline (26.00 g; 0.13 mol) is added to 78 ml (0.71 mol) of acetic anhydride and stirred at room temperature for 5 hours. The reaction is quenched by the addition of 104 ml of water over a 10 minute period, causing the temperature to rise to 43°. The reaction is allowed to cool to room temperature and then cooled to 5° in ice water. The solids are collected by suction filtration, washed with 104 ml of water, and dried to give 2-bromo-4,6-difluoroacetanilide, m.p. 156°.

Cuprous chloride (11.9 g, 0.12 mol) and cupric chloride (16.14 g, 0.12 mol) are dissolved in 100 ml of DMF. 2-Bromo-4,6-difluoroacetanilide (20 g, 0.08 mol) is added and the solution is heated to 130° C. for 20 hours. The reaction is cooled to room temperature and then added dropwise over 30 minutes to 400 ml of 3N HCl. The solid is filtered off, washed with 200 ml of water, and dried to give 2-chloro-4,6-difluoroacetanilide, m.p. 144–150°.

To a slurry of 110.36 g (0.54 mol) of 2-chloro-4,6-difluoroacetanilide in 735 ml of absolute ethanol is added 100.36 ml (1.32 mol) of concentrated HCl. The mixture is heated to reflux for 20 hours and then cooled to room temperature. The mixture is concentrated under reduced pressure to give a residue which is dissolved in 1105 ml of water, and 1N NaOH is added to adjust the pH to 12. The basic mixture is extracted twice with ethyl acetate and the combined organic layers are washed with 735 ml of water. The solvents are evaporated under reduced pressure to give 2-chloro4,6-difluoroaniline as an oil.

A mixture of 4-iodotoluene (210 g, 0.96 mol), 2-chloro-4,6-difluoroaniline (204 g, 1.25 mol), copper powder (36 g, 0.57 mol), cuprous iodide (130 g, 0.68 mol), and potassium carbonate (118 g, 0.86 mol) in 500 ml of xylene is stirred vigorously and heated to reflux in a flask fitted with a Dean-Stark trap for 26 hours. After cooling to room temperature, the solids are filtered off, and the filter cake is washed with 100 ml of xylene. The solvents are evaporated under reduced pressure to give an oil which is dissolved in a mixture of 50 g of silica gel in 750 ml of heptane. The solids are filtered off and the solvents are evaporated under reduced pressure to give N-(2'-chloro-4',6'-difluorophenyl)-4-methylaniline as an oil.

A mixture of 230 g (0.9 mol) N-(2'-chloro-4',6'-difluorophenyl)-4-methylaniline and 325 ml (4.06 mol) of chloroacetyl chloride is heated under a nitrogen atmosphere for one hour at 50°. The solvent is evaporated under reduced pressure to give an oil to which 200 ml of chlorobenzene is added. The solvent is evaporated under reduced pressure to completely remove the chloroacetyl chloride, giving N-(2'-chloro4',6'-difluorophenyl)-N-chloroacetyl-4-methylaniline as an oil.

To a mixture of 100 g (0.3 mol) of N-(2'-chloro-4',6'-difluorophenyl)-N-chloroacetyl-4-methylaniline and 103 g (0.78 mol) of aluminum chloride is added 400 ml of 1,2-dichlorobenzene. The reaction is heated to 140° for 2 hours. The reaction is cooled to room temperature and added to a mixture of 100 ml of concentrated HCl and 700 ml water (cooled to 0–5° in a dry ice/acetone bath). The mixture is extracted twice with 400 ml of methylene chloride. The combined organic layers are washed with 600 ml of 3N HCl. The organic layer is stirred with 66 g of magnesium sulfate and 33 g of charcoal (DARCO G-60). The solids are filtered off and the solvents are evaporated under reduced pressure to give a tan solid which is recrystallized from ethanol to give N-(2'-chloro-4',6'-difluorophenyl)-5-methyloxindole, mp 137–14°.

b) Similarly prepared is 5-methyl-2-(2'-chloro-6'-fluoroanilino)phenylacetic acid of example 1 (d).

The preparation of the starting material, N-(2-chloro-6-fluoro)aniline from 2-chloro-6-fluorobenzamide is described in Rec. Trav. Chim. Pays-Bas, 97, 51–56 (1978).

EXAMPLE 11

A solution of 1300 ml of ethanol, 130 ml of water and 43.5 g of sodium hydroxide is degassed. To the solution is added 100.0 g of N-(2'-chloro-6'-fluorophenyl)-5-methyloxindole and the mixture is heated to 70° for 2 hours. The reaction is cooled to 50° and 90.7 ml of 37% HCl in 453.3 ml of water is added slowly. The suspension is cooled slowly to room temperature and filtered. The filter cake is washed three times with 80 ml of 1:1 ethanol and water and dried to give 5-methyl-2-(2'-chloro-6'-fluoroanilino)phenylacetic acid, m.p. 152–154°.

The starting material, N-(2'-chloro-6'-fluorophenyl)-5-methyloxindole, is prepared in the following manner:

A solution of 261.1 g (2.0 mol) of 1-chloro-3-fluorobenzene in 2000 ml of dry tetrahydrofuran under nitrogen is cooled to −78°. To the solution is added 960 ml (2.4 mol) of 2.5 M n-butyllithium in hexanes over a period of 40 minutes. After stirring for 2.5 hours, a slurry of 155 ml of bromine cooled to −78° is added over 30 minutes and the mixture is stirred for 40 minutes before warming to −10°. The reaction is quenched with an aqueous solution of 151.3 g (1.2 mol) of sodium sulfite and 16.0 g (0.4 mol) of sodium hydroxide in 500 ml of water. The organic layer is separated, the solvents are removed at ambient pressure, and the product is distilled at 92–96° (20 mm Hg) to obtain 2-bromo-3-fluoro-chlorobenzene as a colorless oil.

A mixture of 146.1 g (1.36 mol) of p-toluidine, 12.6 g (0.02 mol) of (±)-2,2'-bis(diphenylphosphino)-1,1'-binaphthyl, 261.9 g (2.73 mol) of sodium t-butoxide, 314.1 g (1.50 mol) of 2-bromo-3-fluoro-chlorobenzene and 6.3 g (0.0069 mol) of tris(dibenzylideneacetone)dipalladium(0) in 3000 ml of toluene is heated to 110° over 30 minutes and stirred an additional 4 hours at this temperature. The mixture is cooled to room temperature and a solution of 680 ml 37% hydrochloric acid and 680 ml of water is added over 15 minutes. The mixture is stirred for 20 minutes and filtered through a pad of Celite. The layers are separated and the organic phase is washed twice with 680 ml of water and once with a solution of 225 g of sodium chloride in 680 ml of water. The solvents are evaporated under reduced pressure to give N-(2'-chloro-6'-fluorophenyl)-4-methylaniline as an oil, b.p. 129–131°/0.5 mm Hg.

A mixture of 25 g (0.11 mol) N-(2'-chloro-6'-fluorophenyl)-4-methylaniline and 40 ml (0.5 mol) of chloroacetylchloride is heated under a nitrogen atmosphere for 15 minutes at 60°. The solvent is evaporated under reduced pressure to give an oil which is dissolved in 25 ml of ethyl acetate. Pentane (250 ml) is added dropwise over 15 minutes to precipitate the product. The mixture is cooled to −15° C. and the solid is filtered and washed with pentane to give N-(2'-chloro-6'-fluorophenyl)-N-chloroacetyl4-methylaniline, m.p. 80–83°.

A mixture of 100 g (0.32 mol) of N-(2'-chloro-6'-fluorophenyl)-N-chloroacetyl-4-methylaniline and 110 g (0.82 mol) of aluminum chloride in 400 ml of 1,2-dichlorobenzene is stirred vigorously and heated to 140° for 7.5 hours. The reaction is cooled to room temperature and added to a mixture of 100 ml of 12N HCl and 700 ml of water (cooled to 0–5° in a dry ice/acetone bath). The mixture is extracted twice with 400 ml of methylene chloride and the combined organic layers are washed with 600 ml of 3N HCl. The organic layer is stirred with 66 g of magnesium sulfate and 33 g of charcoal (DARCO G-60). The solids are filtered through a pad of Celite and the solvents are evaporated under reduced pressure to give a tan solid which is recrystallized from ethanol to give N-(2'-chloro-6'-fluorophenyl)-5-methyloxindole, m.p. 137–140°.

Alternatively, a mixture of 169.8 g of crude N-(2'-chloro-6'-fluorophenyl)-4-methylaniline, 172 ml (2.15 mol) of chloroacetyl chloride in 580 ml of toluene is heated under a nitrogen atmosphere for 2 hours at 70°. The reaction is cooled to room temperature, 450 ml of decane is added, and the volatiles are distilled off under 200 mbar pressure at 62–72°. To the mixture is added 150 ml of toluene and 385 g of aluminum chloride (2.87 mol) slowly at 20–40°. The mixture is heated at 120° for 5 hours, cooled to 20°, and added over 30 minutes to 800 ml of ethyl acetate. The mixture is quenched by addition to a pre-cooled solution of 67 ml of 37% hydrochloric acid in 800 ml of water at 20±10°, and the resultant mixture is filtered through a pad of Celite. The organic layer is separated and the volatiles are distilled off. To the residue is added 100 ml of heptane and the mixture is cooled to 0° over a 30 minute period and stirred for one hour. The mixture is filtered and the filter cake is washed three times with 45 ml of heptane. To the crude product is added 90 g of charcoal (DARCO G-60) and 4500 ml of methanol. The mixture is heated to reflux for two hours, cooled to room temperature, and filtered through a pad of Celite. After distilling off 4390 ml of methanol, the mixture is cooled to 15°. The product is collected by filtration, washed three times with 30 ml of methanol, and dried to give N-(2'-chloro-6'-fluorophenyl)-5-methyloxindole.

What is claimed is:

1. A compound of formula

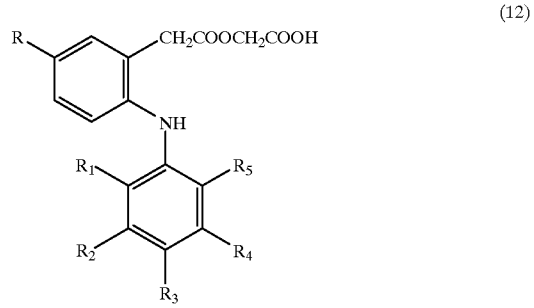

(12)

wherein R is methyl or ethyl;
$R_1$ is chloro or fluoro;
$R_2$ is hydrogen or fluoro;
$R_3$ is hydrogen, fluoro, chloro, methyl, ethyl, methoxy, ethoxy or hydroxy;
$R_4$ is hydrogen or fluoro; and
$R_5$ is chloro, fluoro, trifluoromethyl or methyl;
or a pharmaceutically acceptable salt thereof.

2. A compound according to claim 1 wherein R is methyl or ethyl; $R_1$ is chloro or fluoro; $R_2$ is hydrogen; $R_3$ is hydrogen, fluoro, chloro, methyl or hydroxy; $R_4$ is hydrogen; and $R_5$ is chloro, fluoro or methyl; or a pharmaceutically acceptable salt thereof.

3. A compound according to claim 1 wherein R is methyl or ethyl; $R_1$ is fluoro; $R_2$ is hydrogen; $R_3$ is hydrogen, fluoro or hydroxy; $R_4$ is hydrogen; and $R_5$ is chloro; or a pharmaceutically acceptable salt thereof.

4. A compound according to claim 1 wherein R is methyl or ethyl; $R_1$ is fluoro; $R_2$ is fluoro; $R_3$ is hydrogen, ethoxy or hydroxy; $R_4$ is fluoro; and $R_5$ is fluoro; or a pharmaceutically acceptable salt thereof.

5. A compound according to claim 1 wherein R is methyl or ethyl; $R_1$ is fluoro; $R_2$ is hydrogen; $R_3$ is hydrogen or fluoro; $R_4$ is hydrogen; and $R_5$ is chloro; or a pharmaceutically acceptable salt thereof.

6. A compound according to claim 1 which is carboxymethyl 5-methyl-2-(2'-chloro-6'-fluoroanilino)phenylacetate wherein in formula I R is methyl; $R_1$ is fluoro; $R_2$ is hydrogen; $R_3$ is hydrogen; $R_4$ is hydrogen; and $R_5$ is chloro; or a pharmaceutically acceptable salt thereof.

7. A compound according to claim 1 which is carboxymethyl 5-methyl-2-(2',4'-difluoro-6'-chloroanilino)phenylacetate wherein in formula I R is methyl; $R_1$ is fluoro; $R_2$ is hydrogen; $R_3$ is fluoro; $R_4$ is hydrogen; and $R_5$ is chloro; or a pharmaceutically acceptable salt thereof.

8. A compound according to claim 1 which is carboxymethyl 5-ethyl-2-(2',3',5',6',-tetrafluoroanilino)phenylacetate wherein in formula I R is ethyl; $R_1$ is fluoro; $R_2$ is fluoro; $R_3$ is hydrogen; $R_4$ is fluoro; and $R_5$ is fluoro; or a pharmaceutically acceptable salt thereof.

9. A compound according to claim 1 which is carboxymethyl 5-ethyl-2-(2'4'-dichloro-6'-methylanilino) phenylacetate wherein in formula I R is ethyl; $R_1$ is chloro; $R_2$ is hydrogen; $R_3$ is chloro; $R_4$ is hydrogen; and $R_5$ is methyl; or a pharmaceutically acceptable salt thereof.

10. A pharmaceutical composition comprising an effective antiinflammatory amount of a compound of claim 1 which is substantially free of gastrointestinal ulceration in combination with one or more pharmaceutically acceptable carriers.

11. A pharmaceutical composition comprising an effective antiinflammatory amount of a compound of claim 6 which is substantially free of gastrointestinal ulceration in combination with one or more pharmaceutically acceptable carriers.

12. A pharmaceutical composition comprising an effective antiinflammatory amount of a compound of claim 17 which is substantially free of gastrointestinal ulceration in combination with one or more pharmaceutically acceptable carriers.

13. A pharmaceutical composition comprising an effective antiinflammatory amount of a compound of claim 8 which is substantially free of gastrointestinal ulceration in combination with one or more pharmaceutically acceptable carriers.

14. A pharmaceutical composition comprising an effective antiinflammatory amount of a compound of claim 9 which is substantially free of gastrointestinal ulceration in combination with one or more pharmaceutically acceptable carriers.

15. A method of treating cyclooxygenase dependent disorders in mammals without causing undesirable gastrointestinal side effects which comprises administering to a mammal in need thereof an effective amount of a compound according to claim 1 which is substantially free of gastrointestinal ulceration.

16. A method of treating rheumatoid arthritis, osteoarthritis, pain or inflammation in mammals without causing undesirable gastrointestinal side effects which comprises administering to a mammal in need thereof a correspondingly effective amount of a compound of claim 1 which is substantially free of gastrointestinal ulceration.

17. A method of selectively inhibiting cyclooxygenase-2 activity in a mammal without substantially inhibiting cycloxygenase-1 activity which comprises administering to a mammal in need thereof an effective cyclooxygenase-2 inhibiting amount, which amount is substantially free of cyclooxygenase-1 inhibiting activity, of a compound of formula I

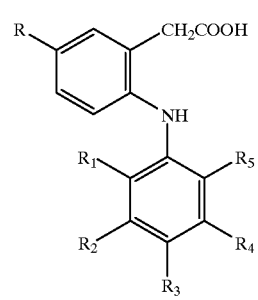

wherein R is methyl or ethyl;
$R_1$ is chloro or fluoro;
$R_2$ is hydrogen or fluoro;
$R_3$ is hydrogen, fluoro, chloro, methyl, ethyl, methoxy or ethoxy;
$R_4$ is hydrogen or fluoro;
$R_5$ is chloro, fluoro or trifluoromethyl;
or a pharmaceutically acceptable salt thereof;
or a pharmaceutically acceptable prodrug ester thereof.

18. A method according to claim 17 wherein the compound is a compound of formula I wherein R is methyl or ethyl; $R_1$ is chloro or fluoro; $R_2$ is hydrogen; $R_3$ is hydrogen, fluoro, chloro or methyl; $R_4$, is hydrogen; and $R_5$ is chloro or fluoro; or a pharmaceutically acceptable salt thereof; or a pharmaceutically acceptable prodrug ester thereof.

19. A method according to claim 17 wherein the compound is a compound of formula I wherein R is methyl or ethyl; $R_1$ is fluoro; $R_2$ is hydrogen; $R_3$ is hydrogen or fluoro; $R_4$ is hydrogen; and $R_5$ is chloro; or a pharmaceutically acceptable salt thereof; or a pharmaceutically acceptable prodrug ester thereof.

20. A method according to claim 17 wherein the compound is a compound of formula I wherein R is methyl or ethyl; $R_1$ is fluoro; $R_2$ is fluoro; $R_3$ is hydrogen or ethoxy; R4 is fluoro; and $R_5$ is fluoro; or a pharmaceutically acceptable salt thereof; or a pharmaceutically acceptable prodrug ester thereof.

21. A method according to claim 17 wherein the compound is a compound of formula I wherein R is methyl; $R_1$ is fluoro; $R_2$ is hydrogen; $R_3$ is hydrogen or fluoro; R4 is hydrogen; and $R_5$ is chloro; or a pharmaceutically acceptable salt thereof; or a pharmaceutically acceptable prodrug ester thereof.

22. A method according to claim 17 wherein the compound is a compound of formula I wherein R is methyl or ethyl; $R_1$ is fluoro; $R_2$–$R_4$ are hydrogen or fluoro; and $R_5$ is chloro or fluoro; or a pharmaceutically acceptable salt thereof; or a pharmaceutically acceptable prodrug ester thereof.

23. A method according to claim 17 wherein the compound is 5-methyl-2-(2'-chloro-6'-fluoroanilino) phenylacetic acid of formula I wherein R is methyl; $R_1$ is fluoro; $R_2$ is hydrogen; $R_3$ is hydrogen; R4 is hydrogen; and $R_5$ is chloro; or a pharmaceutically acceptable salt thereof.

24. A method according to claim 17 wherein the compound is 5-methyl-2-(2',4'-difluoro-6'-chloroanilino) phenylacetic acid of formula I wherein R is methyl; $R_1$ is fluoro; $R_2$ is hydrogen; $R_3$ is fluoro; $R_4$ is hydrogen; and $R_5$ is chloro; or a pharmaceutically acceptable salt thereof.

25. A method according to claim 17 wherein the compound is 5-ethyl-2-(2',3',5',6'-tetrafluoroanilino) phenylacetic acid of formula I wherein R is ethyl; $R_1$ is fluoro; $R_2$ is fluoro; $R_3$ is hydrogen; $R_4$ is fluoro; and $R_5$ is fluoro; or a pharmaceutically acceptable salt thereof.

26. A method according to claim 23 wherein the compound is 5-methyl-2-(2'-chloro-6'-fluoroanilino) phenylacetic acid.

27. A selective cyclooxygenase-2 inhibiting pharmaceutical composition substantially free of cyclooxygenase-1 inhibiting activity comprising an effective cyclooxygenase-2 inhibiting amount, which amount is substantially free of cyclooxygenase-1 inhibiting activity, of a compound of formula I

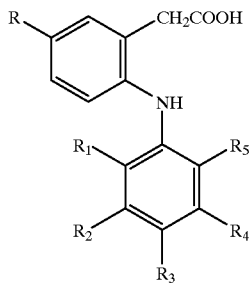

(I)

wherein R is methyl or ethyl;
$R_1$ is chloro or fluoro;
$R_2$ is hydrogen or fluoro;
$R_3$ is hydrogen, fluoro, chloro, methyl, ethyl, methoxy or ethoxy;
$R_4$ is hydrogen or fluoro;
$R_5$ is chloro, fluoro or trifluoromethyl;
or a pharmaceutically acceptable salt thereof;
or a pharmaceutically acceptable prodrug ester thereof;
in combination with one or more pharmaceutically acceptable carriers.

28. A selective cyclooxygenase-2 inhibiting pharmaceutical composition according to claim 27 comprising an effective cyclooxygenase-2 inhibiting amount, which amount is substantially free of cyclooxygenase-1 activity, of a compound of formula I wherein R is methyl or ethyl; $R_1$ is chloro or fluoro; $R_2$ is hydrogen; $R_3$ is hydrogen, fluoro; chloro or methyl; $R_4$ is hydrogen; and $R_5$ is chloro or fluoro; or a pharmaceutically acceptable salt thereof; or a pharmaceutically acceptable prodrug ester thereof; in combination with one or more pharmaceutically acceptable carriers.

29. A selective cyclooxygenase-2 inhibiting pharmaceutical composition according to claim 27 comprising an effective cyclooxygenase-2 inhibiting amount which amount is substantially free of cyclooxygenase-1 inhibiting activity, of a compound of formula I wherein R is methyl or ethyl; $R_1$ is fluoro; $R_2$ is hydrogen; $R_3$ is hydrogen or fluoro; $R_4$ is hydrogen; and $R_5$ is chloro; or a pharmaceutically acceptable salt thereof; or a pharmaceutically acceptable prodrug ester thereof; in combination with one or more pharmaceutically acceptable carriers.

30. A selective cyclooxygenase-2 inhibiting pharmaceutical composition according to claim 27 comprising an effective cyclooxygenase-2 inhibiting amount, which amount is substantially free of cyclooxygenase-1 inhibiting activity, of a compound of formula I wherein R is methyl or ethyl; $R_1$ is fluoro; $R_2$ is fluoro; $R_3$ is hydrogen or ethoxy; $R_4$ is fluoro; and $R_5$ is fluoro; or a pharmaceutically acceptable salt thereof; or a pharmaceutically acceptable prodrug ester thereof; in combination with one or more pharmaceutically acceptable carriers.

31. A selective cyclooxygenase-2 inhibiting pharmaceutical composition according to claim 27 comprising an effective cyclooxygenase-2 inhibiting amount which amount is substantially free of cyclooxygenase-1 inhibiting activity, of a compound of formula I wherein R is methyl; $R_1$ is fluoro; $R_2$ is hydrogen; $R_3$ is hydrogen or fluoro; $R_4$ is hydrogen; and $R_5$ is chloro; or a pharmaceutically acceptable salt thereof; or a pharmaceutically acceptable prodrug ester thereof; in combination with one or more pharmaceutically acceptable carriers.

32. A selective cyclooxygenase-2 inhibiting pharmaceutical composition according to claim 27 comprising an effective cyclooxygenase-2 inhibiting amount which amount is substantially free of cyclooxygenase-1 inhibiting activity, of a compound of formula I wherein R is methyl or ethyl; $R_1$ is fluoro; $R_2$–$R_4$ are hydrogen or fluoro; and $R_5$ is chloro or fluoro; or a pharmaceutically acceptable salt thereof; or a pharmaceutically acceptable prodrug ester thereof; in combination with one or more pharmaceutically acceptable carriers.

33. A selective cyclooxygenase-2 inhibiting pharmaceutical composition according to claim 27 comprising an effective cyclodxygenase-2 inhibiting amount which amount is substantially free of cyclooxygenase-1 inhibiting activity, of 5-methyl-2-(2'-chloro-6'-fluoroanilino)phenylacetic acid of formula I wherein R is methyl; $R_1$ is fluoro; $R_2$ is hydrogen; $R_3$ is hydrogen; $R_4$ is hydrogen; and $R_5$ is chloro; or a pharmaceutically acceptable salt thereof; in combination with one or more pharmaceutically acceptable carriers.

34. A selective cyclooxygenase-2 inhibiting pharmaceutical composition according to claim 27 comprising an effective cyclooxygenase-2 inhibiting amount, which amount is substantially free of cyclooxygenase-1 inhibiting activity, of 5-methyl-2-(2',4'-difluoro-6'-chloroanilino) phenylacetic acid of formula I wherein R is methyl; $R_1$ is fluoro; $R_2$ is hydrogen; $R_3$ is fluoro; $R_4$ is hydrogen; and $R_5$ is chloro; or a pharmaceutically acceptable salt thereof; in combination with one or more pharmaceutically acceptable carriers.

35. A selective cyclooxygenase-2 inhibiting pharmaceutical composition according to claim 27 comprising an effective cyclooxygenase-2 inhibiting amount, which amount is substantially free of cyclooxygenase-1 inhibiting activity, of 5-ethyl-2-(2',3',5',6'-tetrafluoroanilino) phenylacetic acid formula I wherein R is ethyl; $R_1$ is fluoro; $R_2$ is fluoro; $R_3$ is hydrogen; $R_4$ is fluoro; and $R_5$ is fluoro; or a pharmaceutically acceptable salt thereof; in combination with one or more pharmaceutically acceptable carriers.

36. A selective cyclooxygenase-2 inhibiting pharmaceutical composition according to claim 33 comprising an effective cyclooxygenase-2 inhibiting amount, which amount is substantially free of cycloxxygenase-1 inhibiting activity, of 5-methyl-2-(2'-chloro-6'-fluoroanilino) phenylacetic acid; in combination with one or more pharmaceutically acceptable carriers.

* * * * *

UNITED STATES PATENT AND TRADEMARK OFFICE
CERTIFICATE OF CORRECTION

PATENT NO. : 6,291,523 B1  
DATED : September 18, 2001  
INVENTOR(S) : Fujimoto et al.

Page 1 of 1

It is certified that error appears in the above-identified patent and that said Letters Patent is hereby corrected as shown below:

<u>Title page,</u>  
Item [75] should read:  
-- [75] Inventors: Roger A. Fujimoto, Morristown; Leslie W. McQuire, Warren; Benjamin B. Mugrage, Basking Ridge; John H. van Duzer, Asbury, all of NJ (US) --

<u>Column 28,</u>  
Lines 10-25 should read:  
-- 1. A compound of formula

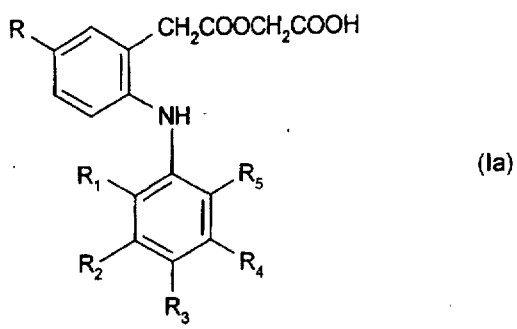

(Ia)

--

<u>Column 29,</u>  
Line 26 should read:  
-- antiinflammatory amount of a compound of claim 7 which --

Signed and Sealed this

Twenty-eighth Day of May, 2002

Attest:

JAMES E. ROGAN  
*Attesting Officer*    *Director of the United States Patent and Trademark Office*